(12) United States Patent
Petry et al.

(10) Patent No.: US 7,453,009 B2
(45) Date of Patent: Nov. 18, 2008

(54) HYDROXYBIPHENYL CARBOXYLIC ACIDS AND DERIVATIVES, METHOD FOR PRODUCING THE SAME AND THEIR USE

(75) Inventors: Stefan Petry, Kelkheim (DE); Karl-Heinz Baringhaus, Wolfersheim (DE); Norbert Tennagels, Siegburg (DE); Gunter Muller, Sulzbach (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 11/759,997

(22) Filed: Jun. 8, 2007

(65) Prior Publication Data

US 2008/0027134 A1    Jan. 31, 2008

Related U.S. Application Data

(63) Continuation of application No. PCT/EP2005/012940, filed on Dec. 2, 2005.

(30) Foreign Application Priority Data

Dec. 16, 2004  (DE)  .................. 10 2004 060 542

(51) Int. Cl.
   *C07C 63/00*  (2006.01)
(52) U.S. Cl. .................. 562/405; 564/155; 514/531; 514/616; 560/45
(58) Field of Classification Search .............. 562/405; 564/155; 514/531, 616; 560/45
   See application file for complete search history.

(56) References Cited

U.S. PATENT DOCUMENTS

| | | | | |
|---|---|---|---|---|
| 5,369,110 | A * | 11/1994 | Schmidlin et al. | 514/281 |
| 6,232,322 | B1 * | 5/2001 | Malamas et al. | 514/303 |
| 6,919,343 | B2 * | 7/2005 | Wood et al. | 514/256 |
| 2005/0004369 | A1 * | 1/2005 | Whitehouse et al. | 548/200 |

FOREIGN PATENT DOCUMENTS

| | | |
|---|---|---|
| WO | WO 99/58518 | 11/1999 |
| WO | WO 2004/099171 | 11/2004 |

* cited by examiner

*Primary Examiner*—Yvonne Eyler
*Assistant Examiner*—Sudhakar Katakam
(74) *Attorney, Agent, or Firm*—Craig M. Bell

(57) ABSTRACT

Disclosed are novel compound of formula I,

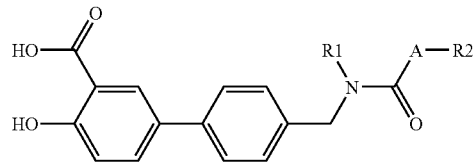

As defined herein and their use as pharmaceutically active compounds for reducing blood glucose, and/or treating one or more of type II diabetes, disturbances of lipid and carbohydrate metabolism, arteriosclerotic manifestations, and insulin resistance.

11 Claims, No Drawings

HYDROXYBIPHENYL CARBOXYLIC ACIDS AND DERIVATIVES, METHOD FOR PRODUCING THE SAME AND THEIR USE

FIELD OF THE INVENTION

The invention relates to substituted hydroxybiphenylcarboxylic acids, and to their physiologically tolerated salts.

BACKGROUND OF THE INVENTION

Compounds of similar structure have been described in the prior art, and their use for the treatment of diabetes has been described in WO 99/58518. Further compounds of similar structure are disclosed in WO 2004/099170, EP 0 490 820 and WO 01/70678.

The invention was based on the object of providing compounds with which it is possible to prevent and treat Diabetes mellitus. The compounds were intended for this purpose to display a therapeutically utilizable blood glucose-lowering effect.

SUMMARY OF THE INVENTION

The object is achieved by providing novel compounds of the formula I,

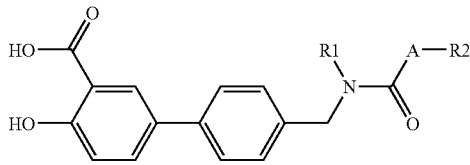

in which:

R1 is selected from —($C_1$-$C_6$)-alkyl, —($C_1$-$C_4$)-alkyl-O—($C_1$-$C_4$)-alkyl, —($C_2$-$C_6$)-alkenyl, —($C_3$-$C_8$)-cycloalkyl, -aryl, —($C_1$-$C_6$)-alkyl-aryl, —($C_2$-$C_6$)-alkenyl-aryl, —($C_1$-$C_6$)-alkyl-cycloalkyl, and —($C_2$-$C_6$)-alkenyl-cycloalkyl, where the alkyl, alkenyl, aryl and cycloalkyl radicals may be substituted by a substituent selected from F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-aryl, and O—CO—($C_1$-$C_6$)-heterocycle; as well as $PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)n-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$-NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, $SO_2$—N(($CH_2$)$_n$-(heterocycle)$_2$ where n may be 0-6, and the aryl radical or heterocyclic radical may be substituted up to twice by a substituent selected from F, Cl, Br, OH, $CF_3$, $NO_2$, CN, $OCF_3$, O—($C_1$-$C_6$)-alkyl, ($C_1$-$C_6$)-alkyl, $NH_2$;

C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl —CO—($C_1$-$C_6$)-alkyl, N($C_1$-$C_6$)-alkyl N($C_1$-$C_6$)-alkyl —CO-aryl, N($C_1$-$C_6$)-alkyl —CO-heterocycle, N($C_1$-$C_6$)-alkyl —COO-aryl, N($C_1$-$C_6$)-alkyl —COO-heterocycle, N($C_1$-$C_6$)-alkyl —CO—NH—($C_1$-$C_6$)-alkyl), N($C_1$-$C_6$)-alkyl —CO—NH-aryl, N($C_1$-$C_6$)-alkyl —CO—NH-heterocycle, N(($C_1$-$C_6$)-alkyl)-CO—N—($C_1$-$C_6$)-alkyl)$_2$, N(($C_1$-$C_6$)-alkyl)-CO-N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N-($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl, and O—($CH_2$)$_n$-heterocycle, where n may be 0-6, where the aryl radical or heterocyclic radical may be substituted one to 3 times by a substituent selected from F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, and $CONH_2$;

R2 is selected from —($C_1$-$C_6$)-alkyl, —($C_1$-$C_4$)-alkyl-O—($C_1$-$C_4$)-alkyl, —($C_2$-$C_6$)-alkenyl, —($C_3$-$C_8$)-cycloalkyl, —($C_1$-$C_6$)-alkyl-aryl, —($C_2$-$C_6$)-alkenyl-aryl, heterocycle, —($C_1$-$C_6$)-alkyl-heterocycle, —($C_2$-$C_6$)-alkenyl-heterocycle, —($C_1$-$C_6$)-alkyl-cycloalkyl, and —($C_2$-$C_6$)-alkenyl-cycloalkyl, where the alkyl, alkenyl, aryl, heterocyclyl and cycloalkyl radicals may be substituted by a substituent selected from F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-aryl, and O—CO—($C_1$-$C_6$)-heterocycle; as well as $PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, and $SO_2$—N(($CH_2$)$_n$-(heterocycle)$_2$, where n may be 0-6, and the aryl radical or heterocyclic radical may be substituted up to twice by a substituent selected from F, Cl, Br, OH, $CF_3$, $NO_2$, CN, $OCF_3$, O—($C_1$-$C_6$)-alkyl, ($C_1$-$C_6$)-alkyl, and $NH_2$; as well as C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl —CO—($C_1$-$C_6$)-alkyl, N($C_1$-$C_6$)-alkyl —COO—($C_1$-$C_6$)-alkyl, N($C_1$-$C_6$)-alkyl —CO-aryl, N($C_1$-$C_6$)-alkyl —CO-heterocycle, N($C_1$-$C_6$)-alkyl —COO-aryl, N($C_1$-$C_6$)-alkyl —COO-heterocycle, N($C_1$-$C_6$)-alkyl — CO—NH—($C_1$-$C_6$)-alkyl), N($C_1$-$C_6$)-alkyl — CO—NH-aryl, N($C_1$-$C_6$)-alkyl —CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-

(heterocycle)$_2$, N(aryl)-CO—(C$_1$-C$_6$)-alkyl, N(heterocycle)-CO—(C$_1$-C$_6$)-alkyl, N(aryl)-COO—(C$_1$-C$_6$)-alkyl, N(heterocycle)-COO—(C$_1$-C$_6$)-alkyl, N(aryl)-CO-aryl, N(heterocycle)-CO-aryl, N(aryl)-COO-aryl, N(heterocycle)-COO-aryl, N(aryl)-CO—NH—(C$_1$-C$_6$)-alkyl), N(heterocycle)-CO—NH—(C$_1$-C$_6$)-alkyl), N(aryl)-CO—NH-aryl, N(heterocycle)-CO—NH-aryl, N(aryl)-CO—N—(C$_1$-C$_6$)-alkyl)$_2$, N(heterocycle)-CO—N—(C$_1$-C$_6$)-alkyl)$_2$, N(aryl)-CO—N((C$_1$-C$_6$)-alkyl)-aryl, N(heterocycle)-CO—N((C$_1$-C$_6$)-alkyl)-aryl, N(aryl)-CO—N-(aryl)$_2$, N(heterocycle)-CO—N-(aryl)$_2$, aryl, O—(CH$_2$)$_n$-aryl, and O—(CH$_2$)$_n$-heterocycle, where n may be 0-6, where the aryl radical or heterocyclic radical may be substituted one to 3 times by a substituent selected from F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$-CH$_3$, COOH, COO—(C$_1$-C$_6$)-alkyl, and CONH$_2$;

A is selected from a bond, O, NH, and S;

and the physiologically tolerated salts thereof.

DETAILED DESCRIPTION

Preference is given to compounds of the formula I in which the radicals R1, R2 and A have the following meaning:

R1 is selected from —(C$_1$-C$_6$)-alkyl, —(C$_1$-C$_4$)-alkyl-O—(C$_1$-C$_4$)-alkyl, —(C$_2$-C$_6$)-alkenyl, —(C$_3$-C$_8$)-cycloalkyl, -aryl, —(C$_1$-C$_6$)-alkyl-aryl, —(C$_2$-C$_6$)-alkenyl-aryl, —(C$_1$-C$_6$)-alkyl-cycloalkyl, and —(C$_2$-C$_6$)-alkenyl-cycloalkyl, where the alkyl, alkenyl, aryl and cycloalkyl radicals may be substituted by a substituent selected from F, Cl, Br, I, (C$_1$-C$_6$)alkyl, O—(C$_1$-C$_6$)-alkyl;

R2 is selected from —(C$_1$-C$_6$)-alkyl, —(C$_1$-C$_4$)-alkyl-O—(C$_1$-C$_4$)-alkyl, —(C$_2$-C$_6$)-alkenyl, —(C$_3$-C$_8$)-cycloalkyl, —(C$_1$-C$_6$)-alkyl-aryl, —(C$_2$-C$_6$)-alkenyl-aryl, heterocycle, —(C$_1$-C$_6$)-alkyl-heterocycle, —(C$_2$-C$_6$)-alkenyl-heterocycle, —(C$_1$-C$_6$)-alkyl-cycloalkyl, and —(C$_2$-C$_6$)-alkenyl-cycloalkyl, where the alkyl, alkenyl, aryl, heterocyclyl and cycloalkyl radicals may be substituted by a substituent selected from F, Cl, Br, I, (C$_1$-C$_6$)alkyl, and O—(C$_1$-C$_6$)-alkyl; and A is a bond;

and the physiologically tolerated salts thereof.

Particular preference is given to compounds of the formula I in which the radicals R1, R2 and A have the following meanings:

R1 is selected from —(C$_1$-C$_6$)-alkyl, —(C$_1$-C$_6$)-alkyl-phenyl, —(C$_1$-C$_6$)-alkyl—(C$_3$-C$_8$)-cycloalkyl, and —(C$_3$-C$_8$)-cycloalkyl, where the alkyl, phenyl and cycloalkyl radicals may be substituted by a substituent selected from F, Cl, Br, I, (C$_1$-C$_6$)alkyl, and O—(C$_1$-C$_6$)-alkyl;

R2 is selected from —(C$_1$-C$_6$)-alkyl, —(C$_1$-C$_6$)-alkyl-phenyl, —(C$_1$-C$_6$)-alkyl—(C$_3$-C$_8$)-cycloalkyl, —(C$_3$-C$_8$) cycloalkyl, —(C$_2$-C$_6$)-alkenyl-phenyl, and -heterocycle, where the alkyl, phenyl, heterocyclyl and cycloalkyl radicals may be substituted by a substituent selected from F, Cl, Br, I, (C$_1$-C$_6$)alkyl, and O—(C$_1$-C$_6$)-alkyl; and A is a bond;

and the physiologically tolerated salts thereof.

Very particular preference is given to compounds of the formula I in which the radicals R1, R2 and A have the following meanings:

R1 is selected from —CH$_2$-phenyl, —CH$_2$—(C$_3$-C$_8$)-cycloalkyl, —(C$_3$-C$_8$)-cycloalkyl, where the phenyl and cycloalkyl radicals may be substituted by F, Cl, Br, I, (C$_1$-C$_6$)alkyl, and O—(C$_1$-C$_6$)-alkyl;

R2 is selected from —CH$_2$-phenyl, —CH$_2$—(C$_3$-C$_8$)-cycloalkyl, —(C$_3$-C$_8$)-cycloalkyl, —(C$_2$-C$_6$)-alkenyl-phenyl, —CH$_2$-heterocycle, -heterocycle, where the phenyl, heterocyclyl and cycloalkyl radicals may be substituted by F, Cl, Br, I, (C$_1$-C$_6$)alkyl, O—(C$_1$-C$_6$)-alkyl; and A is a bond;

and the physiologically tolerated salts thereof.

The invention relates to compounds of the formula I in the form of their racemates, racemic mixtures and pure enantiomers and to their diastereomers and mixtures thereof.

If radicals or substituents may occur more than once in the compounds of the formula I, they may all, independently of one another, have the stated meanings and be identical or different. Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydro-chloric acid, hydrobromic, phosphoric, metaphosphoric, nitric and sulfuric acid, and of organic acids such as, for example, acetic acid, benzenesulfonic, benzoic, citric, ethane-sulfonic, fumaric, gluconic, glycolic, isethionic, lactic, lactobionic, maleic, malic, methane-sulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compounds of formula I" hereinafter refer to compounds of the formula I as described above, and their salts, solvates and physiologically functional derivatives as described herein.

An alkyl radical means a straight-chain or branched hydrocarbon chain having one or more carbons, such as, for example, methyl, ethyl, isopropyl, tert-butyl, hexyl.

The alkyl radicals may be substituted one or more times by suitable groups such as, for example: F, Cl, Br, I, CF$_3$, NO$_2$, N$_3$, CN, COOH, COO(C$_1$-C$_6$)alkyl, CONH$_2$, CONH(C$_1$-C$_6$) alkyl, CON[(C$_1$-C$_6$)alkyl]$_2$, cycloalkyl, (C$_2$-C$_6$)-alkenyl, $(C_2-C_6)$-alkynyl, O—$(C_1-C_6)$-alkyl O—CO—$(C_1-C_6)$-alkyl, O—CO—$(C_1-C_6)$-aryl, O—CO—$(C_1-C_6)$-heterocycle;

$PO_3H_2$, $SO_3H$, $SO_2$—$NH_2$, $SO_2NH(C_1-C_6)$-alkyl, $SO_2N[(C_1-C_6)$-alkyl$]_2$, S—$(C_1-C_6)$-alkyl, S—$(CH_2)_n$-aryl, S—$(CH_2)_n$-heterocycle, SO—$(C_1-C_6)$-alkyl, SO—$(CH_2)_n$-aryl, SO—$(CH_2)_n$-heterocycle, $SO_2$—$(C_1-C_6)$-alkyl, $SO_2$—$(CH_2)_n$-aryl, $SO_2$—$(CH_2)_n$-heterocycle, $SO_2$—NH$(CH_2)_n$-aryl, $SO_2$—NH$(CH_2)_n$-heterocycle, $SO_2$—N$(C_1-C_6)$-alkyl)$(CH_2)_n$-aryl, $SO_2$—N$(C_1-C_6)$-alkyl)$(CH_2)_n$-heterocycle, $SO_2$—N$((CH_2)_n$-aryl$)_2$, $SO_2$—N$((CH_2)_n$-(heterocycle)$)_2$ where n may be 0-6, and the aryl radical or heterocyclic radical may be substituted up to twice by F, Cl, Br, OH, $CF_3$, $NO_2$, CN, $OCF_3$, O—$(C_1-C_6)$-alkyl, $(C_1-C_6)$-alkyl, $NH_2$;

$C(NH)(NH_2)$, $NH_2$, NH—$(C_1-C_6)$-alkyl, N$((C_1-C_6)$-alkyl$)_2$, NH$(C_1-C_7)$-acyl, NH—CO—$(C_1-C_6)$-alkyl, NH—COO—$(C_1-C_6)$-alkyl, NH—CO-aryl, NH—CO-heterocycle, NH—COO-aryl, NH—COO-heterocycle, NH—CO—NH—$(C_1-C_6)$-alkyl, NH—CO—NH-aryl, NH—CO—NH-heterocycle, N$(C_1-C_6)$-alkyl —CO—$(C_1-C_6)$-alkyl, N$(C_1-C_6)$-alkyl —COO—$(C_1-C_6)$-alkyl, N$(C_1-C_6)$-alkyl —CO-aryl, N$(C_1-C_6)$-alkyl —CO-heterocycle, N$(C_1-C_6)$-alkyl —COO-aryl, N$(C_1-C_6)$-alkyl —COO-heterocycle, N$(C_1-C_6)$-alkyl —CO—NH—$(C_1-C_6)$-alkyl), N$(C_1-C_6)$-alkyl —CO—NH-aryl, N$(C_1-C_6)$-alkyl —CO—NH-heterocycle, N$((C_1-C_6)$-alkyl)-CO—N—$(C_1-C_6)$-alkyl$)_2$, N$((C_1-C_6)$-alkyl)-CO—N$((C_1-C_6)$-alkyl)-aryl, N$((C_1-C_6)$-alkyl)-CO—N$((C_1-C_6)$-alkyl)-heterocycle, N$((C_1-C_6)$-alkyl)-CO—N-(aryl)$_2$, N$((C_1-C_6)$-alkyl)-CO—N-(heterocycle)$_2$, N(aryl)-CO—$(C_1-C_6)$-alkyl, N(heterocycle)-CO—$(C_1-C_6)$-alkyl, N(aryl)-COO—$(C_1-C_6)$-alkyl, N(heterocycle)-COO—$(C_1-C_6)$-alkyl, N(aryl)-CO-aryl, N(heterocycle)-CO-aryl, N(aryl)-COO-aryl, N(heterocycle)-COO-aryl, N(aryl)-CO—NH—$(C_1-C_6)$-alkyl), N(heterocycle)-CO—NH—$(C_1-C_6)$-alkyl), N(aryl)-CO—NH-aryl, N(heterocycle)-CO—NH-aryl, N(aryl)-CO—N—$(C_1-C_6)$-alkyl$)_2$, N(heterocycle)-CO—N—$(C_1-C_6)$-alkyl$)_2$, N(aryl)-CO—N$((C_1-C_6)$-alkyl)-aryl, N(heterocycle)-CO—N$((C_1-C_6)$-alkyl)-aryl, N(aryl)-CO—N-(aryl)$_2$, N(heterocycle)-CO—N-(aryl)$_2$, aryl, O—$(CH_2)_n$-aryl, O—$(CH_2)_n$-heterocycle, where n may be 0-6, where the aryl radical or heterocyclic radical may be substituted one to 3 times by F, Cl, Br, I, OH, $CF_3$, $NO_2$, CN, $OCF_3$, O—$(C_1-C_6)$-alkyl, $(C_1-C_6)$-alkyl, $NH_2$, NH$(C_1-C_6)$-alkyl, N$((C_1-C_6)$-alkyl$)_2$, $SO_2$-$CH_3$, COOH, COO—$(C_1-C_6)$-alkyl, $CONH_2$.

An alkenyl radical means a straight-chain or branched hydrocarbon chain having two or more carbons and one or more double bonds, such as, for example, vinyl, allyl, pentenyl.

The alkenyl radicals may be substituted one or more times by suitable groups such as, for example: F, Cl, Br, I, $CF_3$, $NO_2$, $N_3$, CN, COOH, COO$(C_1-C_6)$alkyl, $CONH_2$, CONH$(C_1-C_6)$alkyl, CON$[(C_1-C_6)$alkyl$]_2$, cycloalkyl, $(C_1-C_{10})$-alkyl, $(C_2-C_6)$-alkynyl, O—$(C_1-C_6)$-alkyl O—CO—$(C_1-C_6)$-alkyl, O—CO—$(C_1-C_6)$-aryl, O—CO—$(C_1-C_6)$-heterocycle;

$PO_3H_2$, $SO_3H$, $SO_2$—$NH_2$, $SO_2NH(C_1-C_6)$-alkyl, $SO_2N[(C_1-C_6)$-alkyl$]_2$, S—$(C_1-C_6)$-alkyl, S—$(CH_2)_n$-aryl, S—$(CH_2)_n$-heterocycle, SO—$(C_1-C_6)$-alkyl, SO—$(CH_2)_n$- aryl, SO—$(CH_2)_n$-heterocycle, $SO_2$—$(C_1-C_6)$-alkyl, $SO_2$—$(CH_2)_n$-aryl, $SO_2$—$(CH_2)_n$-heterocycle, $SO_2$—NH$(CH_2)_n$-aryl, $SO_2$—NH$(CH_2)_n$-heterocycle, $SO_2$—N$(C_1-C_6)$-alkyl)$(CH_2)_n$-aryl, $SO_2$—N$(C_1-C_6)$-alkyl)$(CH_2)_n$-heterocycle, $SO_2$—N$((CH_2)_n$-aryl$)_2$, $SO_2$—N$((CH_2)_n$-(heterocycle)$)_2$ where n may be 0-6, and the aryl radical or heterocyclic radical may be substituted up to twice by F, Cl, Br, OH, $CF_3$, $NO_2$, CN, $OCF_3$, O—$(C_1-C_6)$-alkyl, $(C_1-C_6)$-alkyl, $NH_2$;

$C(NH)(NH_2)$, $NH_2$, NH—$(C_1-C_6)$-alkyl, N$((C_1-C_6)$-alkyl$)_2$, NH$(C_1-C_7)$-acyl, NH—CO—$(C_1-C_6)$-alkyl, NH—COO—$(C_1-C_6)$-alkyl, NH—CO-aryl, NH—CO-heterocycle, NH—COO-aryl, NH—COO-heterocycle, NH—CO—NH—$(C_1-C_6)$-alkyl, NH—CO—NH-aryl, NH—CO—NH-heterocycle, N$(C_1-C_6)$-alkyl —CO—$(C_1-C_6)$-alkyl, N$(C_1-C_6)$-alkyl —COO—$(C_1-C_6)$-alkyl, N$(C_1-C_6)$-alkyl —CO-aryl, N$(C_1-C_6)$-alkyl —CO-heterocycle, N$(C_1-C_6)$-alkyl —COO-aryl, N$(C_1-C_6)$-alkyl —COO-heterocycle, N$(C_1-C_6)$-alkyl —CO—NH—$(C_1-C_6)$-alkyl), N$(C_1-C_6)$-alkyl —CO—NH-aryl, N$(C_1-C_6)$-alkyl —CO—NH-heterocycle, N$((C_1-C_6)$-alkyl)-CO—N—$(C_1-C_6)$-alkyl$)_2$, N$((C_1-C_6)$-alkyl)-CO—N$((C_1-C_6)$-alkyl)-aryl, N$((C_1-C_6)$-alkyl)-CO—N$((C_1-C_6)$-alkyl)-heterocycle, N$((C_1-C_6)$-alkyl)-CO—N-(aryl)$_2$, N$((C_1-C_6)$-alkyl)-CO—N-(heterocycle)$_2$, N(aryl)-CO—$(C_1-C_6)$-alkyl, N(heterocycle)-CO—$(C_1-C_6)$-alkyl, N(aryl)-COO—$(C_1-C_6)$-alkyl, N(heterocycle)-COO—$(C_1-C_6)$-alkyl, N(aryl)-CO-aryl, N(heterocycle)-CO-aryl, N(aryl)-COO-aryl, N(heterocycle)-COO-aryl, N(aryl)-CO—NH—$(C_1-C_6)$-alkyl), N(heterocycle)-CO—NH—$(C_1-C_6)$-alkyl), N(aryl)-CO—NH-aryl, N(heterocycle)-CO—NH-aryl, N(aryl)-CO—N—$(C_1-C_6)$-alkyl$)_2$, N(heterocycle)-CO—N—$(C_1-C_6)$-alkyl$)_2$, N(aryl)-CO—N$((C_1-C_6)$-alkyl)-aryl, N(heterocycle)-CO—N$((C_1-C_6)$-alkyl)-aryl, N(aryl)-CO—N-(aryl)$_2$, N(heterocycle)-CO—N-(aryl)$_2$, aryl, O—$(CH_2)_n$-aryl, O—$(CH_2)_n$-heterocycle, where n may be 0-6, where the aryl radical or heterocyclic radical may be substituted one to 3 times by F, Cl, Br, I, OH, $CF_3$, $NO_2$, CN, $OCF_3$, O—$(C_1-C_6)$-alkyl, $(C_1-C_6)$-alkyl, $NH_2$, NH$(C_1-C_6)$-alkyl, N$((C_1-C_6)$-alkyl$)_2$, $SO_2$-$CH_3$, COOH, COO—$(C_1-C_6)$-alkyl, $CONH_2$.

An alkynyl radical means a straight-chain or branched hydrocarbon chain having two or more carbons and one or more triple bonds, such as, for example, ethynyl, propynyl, hexynyl.

The alkynyl radicals may be substituted one or more times by suitable groups such as, for example: F, Cl, Br, I, $CF_3$, $NO_2$, $N_3$, CN, COOH, COO$(C_1-C_6)$alkyl, $CONH_2$, CONH$(C_1-C_6)$alkyl, CON$[(C_1-C_6)$alkyl$]_2$, cycloalkyl, $(C_2-C_6)$-alkenyl, $(C_1-C_{10})$-alkyl, O—$(C_1-C_6)$-alkyl O—CO—$(C_1-C_6)$-alkyl, O—CO—$(C_1-C_6)$-aryl, O—CO—$(C_1-C_6)$-heterocycle;

$PO_3H_2$, $SO_3H$, $SO_2$—$NH_2$, $SO_2NH(C_1-C_6)$-alkyl, $SO_2N[(C_1-C_6)$-alkyl$]_2$, S—$(C_1-C_6)$-alkyl, S—$(CH_2)_n$-aryl, S—$(CH_2)_n$-heterocycle, SO—$(C_1-C_6)$-alkyl, SO—$(CH_2)_n$-aryl, SO—$(CH_2)_n$-heterocycle, $SO_2$—$(C_1-C_6)$-alkyl, $SO_2$—$(CH_2)_n$-aryl, $SO_2$—$(CH_2)_n$-heterocycle, $SO_2$—NH$(CH_2)_n$-aryl, $SO_2$—NH$(CH_2)_n$-heterocycle, $SO_2$—N$(C_1-C_6)$-alkyl)$(CH_2)_n$-aryl, $SO_2$—N$(C_1-C_6)$-alkyl)$(CH_2)_n$-heterocycle, $SO_2$—N$((CH_2)_n$-aryl$)_2$, $SO_2$—N$((CH_2)_n$-(heterocycle)$)_2$ where n may be 0-6, and the aryl radical or heterocyclic radical may be substituted up to twice by F, Cl, Br, OH, $CF_3$, $NO_2$, CN, $OCF_3$, O—$(C_1-C_6)$-alkyl, $(C_1-C_6)$-alkyl, $NH_2$;

$C(NH)(NH_2)$, $NH_2$, NH—$(C_1-C_6)$-alkyl, N$((C_1-C_6)$-alkyl$)_2$, NH$(C_1-C_7)$-acyl, NH—CO—$(C_1-C_6)$-alkyl, NH—COO—$(C_1-C_6)$-alkyl, NH—CO-aryl, NH—CO-heterocycle, NH—COO-aryl, NH—COO-heterocycle, NH—CO—NH—$(C_1-C_6)$-alkyl, NH—CO—NH-aryl, NH—CO—NH-heterocycle, N$(C_1-C_6)$-alkyl —CO—$(C_1-C_6)$-alkyl, N$(C_1-C_6)$-alkyl —COO—$(C_1-C_6)$-alkyl, N$(C_1-C_6)$-alkyl —CO-aryl, N$(C_1-C_6)$-alkyl —CO-heterocycle, N$(C_1-C_6)$-alkyl —COO-aryl, N$(C_1-C_6)$-alkyl —COO-heterocycle, $N(C_1$-$C_6)$-alkyl —CO—NH—$(C_1$-$C_6)$-alkyl), $N(C_1$-$C_6)$-alkyl —CO—NH-aryl, $N(C_1$-$C_6)$-alkyl —CO—NH-heterocycle, $N((C_1$-$C_6)$-alkyl)-CO—N—$(C_1$-$C_6)$-alkyl)$_2$, $N((C_1$-$C_6)$-alkyl)-CO—N($(C_1$-$C_6)$-alkyl)-aryl, $N((C_1$-$C_6)$-alkyl)-CO—N($(C_1$-$C_6)$-alkyl)-heterocycle, $N((C_1$-$C_6)$-alkyl)-CO—N-(aryl)$_2$, $N((C_1$-$C_6)$-alkyl)-CO—N-(heterocycle)$_2$, N(aryl)-CO—$(C_1$-$C_6)$-alkyl, N(heterocycle)-CO—$(C_1$-$C_6)$-alkyl, N(aryl)-COO—$(C_1$-$C_6)$-alkyl, N(heterocycle)-COO—$(C_1$-$C_6)$-alkyl, N(aryl)-CO-aryl, N(heterocycle)-CO-aryl, N(aryl)-COO-aryl, N(heterocycle)-COO-aryl, N(aryl)-CO—NH—$(C_1$-$C_6)$-alkyl), N(heterocycle)-CO—NH—$(C_1$-$C_6)$-alkyl), N(aryl)-CO—NH-aryl, N(heterocycle)-CO—NH-aryl, N(aryl)-CO—N—$(C_1$-$C_6)$-alkyl)$_2$, N(heterocycle)-CO—N—$(C_1$-$C_6)$-alkyl)$_2$, N(aryl)-CO—N($(C_1$-$C_6)$-alkyl)-aryl, N(heterocycle)-CO—N($(C_1$-$C_6)$-alkyl)-aryl, N(aryl)-CO—N-(aryl)$_2$, N(heterocycle)-CO—N-(aryl)$_2$, aryl, O—$(CH_2)_n$-aryl, O—$(CH_2)_n$-heterocycle, where n may be 0-6, where the aryl radical or heterocyclic radical may be substituted one to 3 times by F, Cl, Br, I, OH, $CF_3$, $NO_2$, CN, $OCF_3$, O—$(C_1$-$C_6)$-alkyl, $(C_1$-$C_6)$-alkyl, $NH_2$, $NH(C_1$-$C_6)$-alkyl, $N((C_1$-$C_6)$-alkyl)$_2$, $SO_2$-$CH_3$, COOH, COO—$(C_1$-$C_6)$-alkyl, $CONH_2$.

An aryl radical means a phenyl, naphthyl-, biphenyl-, tetrahydronaphthyl-, alpha- or beta- tetralon-, indanyl- or indan-1-on-yl radical.

The aryl radicals may be substituted one or more times by suitable groups such as, for example: F, Cl, Br, I, $CF_3$, $NO_2$, $N_3$, CN, COOH, $COO(C_1$-$C_6)$alkyl, $CONH_2$, $CONH(C_1$-$C_6)$alkyl, $CON[(C_1$-$C_6)$alkyl]$_2$, cycloalkyl, $(C_1$-$C_{10})$-alkyl, $(C_2$-$C_6)$-alkenyl, $(C_2$-$C_6)$-alkynyl, O—$(C_1$-$C_6)$-alkyl O—CO—$(C_1$-$C_6)$-alkyl, O—CO—$(C_1$-$C_6)$-aryl, O—CO—$(C_1$-$C_6)$-heterocycle;

$PO_3H_2$, $SO_3H$, $SO_2$—$NH_2$, $SO_2NH(C_1$-$C_6)$-alkyl, $SO_2N[(C_1$-$C_6)$-alkyl]$_2$, S—$(C_1$-$C_6)$-alkyl, S—$(CH_2)_n$-aryl, S—$(CH_2)_n$-heterocycle, SO—$(C_1$-$C_6)$-alkyl, SO—$(CH_2)_n$-aryl, SO—$(CH_2)_n$-heterocycle, $SO_2$—$(C_1$-$C_6)$-alkyl, $SO_2$—$(CH_2)_n$-aryl, $SO_2$—$(CH_2)_n$-heterocycle, $SO_2$—$NH(CH_2)_n$-aryl, $SO_2$—$NH(CH_2)_n$-heterocycle, $SO_2$—$N(C_1$-$C_6)$-alkyl)$(CH_2)_n$-aryl, $SO_2$—$N(C_1$-$C_6)$-alkyl)$(CH_2)_n$-heterocycle, $SO_2$—$N((CH_2)_n$-aryl)$_2$, $SO_2$—$N((CH_2)_n$-(heterocycle)$_2$ where n may be 0-6, and the aryl radical or heterocyclic radical may be substituted up to twice by F, Cl, Br, OH, $CF_3$, $NO_2$, CN, $OCF_3$, O—$(C_1$-$C_6)$-alkyl, $(C_1$-$C_6)$-alkyl, $NH_2$;

$C(NH)(NH_2)$, $NH_2$, NH—$(C_1$-$C_6)$-alkyl, $N((C_1$-$C_6)$-alkyl)$_2$, $NH(C_1$-$C_7)$-acyl, NH—CO—$(C_1$-$C_6)$-alkyl, NH—COO—$(C_1$-$C_6)$-alkyl, NH—CO-aryl, NH—CO-heterocycle, NH—COO-aryl, NH—COO-heterocycle, NH—CO—NH—$(C_1$-$C_6)$-alkyl, NH—CO—NH-aryl, NH—CO—NH-heterocycle, $N(C_1$-$C_6)$-alkyl —CO—$(C_1$-$C_6)$-alkyl, $N(C_1$-$C_6)$-alkyl —COO—$(C_1$-$C_6)$-alkyl, $N(C_1$-$C_6)$-alkyl —CO-aryl, $N(C_1$-$C_6)$-alkyl —CO-heterocycle, $N(C_1$-$C_6)$-alkyl —COO-aryl, $N(C_1$-$C_6)$-alkyl —COO-heterocycle, $N(C_1$-$C_6)$-alkyl —CO—NH—$(C_1$-$C_6)$-alkyl), $N(C_1$-$C_6)$-alkyl —CO—NH-aryl, $N(C_1$-$C_6)$-alkyl —CO—NH-heterocycle, $N((C_1$-$C_6)$-alkyl)-CO—N—$(C_1$-$C_6)$-alkyl)$_2$, $N((C_1$-$C_6)$-alkyl)-CO—N($(C_1$-$C_6)$-alkyl)-aryl, $N((C_1$-$C_6)$-alkyl)-CO—N($(C_1$-$C_6)$-alkyl)-heterocycle, $N((C_1$-$C_6)$-alkyl)-CO—N-(aryl)$_2$, $N((C_1$-$C_6)$-alkyl)-CO—N-(heterocycle)$_2$, N(aryl)-CO—$(C_1$-$C_6)$-alkyl, N(heterocycle)-CO—$(C_1$-$C_6)$-alkyl, N(aryl)-COO—$(C_1$-$C_6)$-alkyl, N(heterocycle)-COO—$(C_1$-$C_6)$-alkyl, N(aryl)-CO-aryl, N(heterocycle)-CO-aryl, N(aryl)-COO-aryl, N(heterocycle)-COO-aryl, N(aryl)-CO—NH—$(C_1$-$C_6)$-alkyl), N(heterocycle)-CO—NH—$(C_1$-$C_6)$-alkyl), N(aryl)-CO—NH-aryl, N(heterocycle)-CO—NH-aryl, N(aryl)-CO—N—$(C_1$-$C_6)$-alkyl)$_2$, N(heterocycle)-CO—N—$(C_1$-$C_6)$-alkyl)$_2$, N(aryl)-CO—N($(C_1$-$C_6)$-alkyl)-aryl, N(heterocycle)-CO—N($(C_1$-$C_6)$-alkyl)-aryl, N(aryl)-CO—N-(aryl)$_2$, N(heterocycle)-CO—N-(aryl)$_2$, aryl, O—$(CH_2)_n$-aryl, O—$(CH_2)_n$-heterocycle, where n may be 0-6, where the aryl radical or heterocyclic radical may be substituted one to 3 times by F, Cl, Br, I, OH, $CF_3$, $NO_2$, CN, $OCF_3$, O—$(C_1$-$C_6)$-alkyl, $(C_1$-$C_6)$-alkyl, $NH_2$, $NH(C_1$-$C_6)$-alkyl, $N((C_1$-$C_6)$-alkyl)$_2$, $SO_2$-$CH_3$, COOH, COO—$(C_1$-$C_6)$-alkyl, $CONH_2$.

A cycloalkyl radical means a ring system which comprises one or more rings, which is in saturated or partially unsaturated (with one or two double bonds) form and which is composed exclusively of carbon atoms, such as, for example, cyclopropyl, cyclopentyl, cyclopentenyl, cyclohexyl or adamantyl.

The cycloalkyl radicals radicals may be substituted one or more times by suitable groups such as, for example: F, Cl, Br, I, $CF_3$, $NO_2$, $N_3$, CN, COOH, $COO(C_1$-$C_6)$alkyl, $CONH_2$, $CONH(C_1$-$C_6)$alkyl, $CON[(C_1$-$C_6)$alkyl]$_2$, cycloalkyl, $(C_1$-$C_{10})$-alkyl, $(C_2$-$C_6)$-alkenyl, $(C_2$-$C_6)$-alkynyl, O—$(C_1$-$C_6)$-alkyl O—CO—$(C_1$-$C_6)$-alkyl, O—CO—$(C_1$-$C_6)$-aryl, O—CO—$(C_1$-$C_6)$-heterocycle;

$PO_3H_2$, $SO_3H$, $SO_2$—$NH_2$, $SO_2NH(C_1$-$C_6)$-alkyl, $SO_2N[(C_1$-$C_6)$-alkyl]$_2$, S—$(C_1$-$C_6)$-alkyl, S—$(CH_2)_n$-aryl, S—$(CH_2)_n$-heterocycle, SO—$(C_1$-$C_6)$-alkyl, SO—$(CH_2)_n$-aryl, SO—$(CH_2)_n$-heterocycle, $SO_2$—$(C_1$-$C_6)$-alkyl, $SO_2$—$(CH_2)_n$-aryl, $SO_2$—$(CH_2)_n$-heterocycle, $SO_2$—$NH(CH_2)_n$-aryl, $SO_2$—$NH(CH_2)_n$-heterocycle, $SO_2$—$N(C_1$-$C_6)$-alkyl)$(CH_2)_n$-aryl, $SO_2$—$N(C_1$-$C_6)$-alkyl)$(CH_2)_n$-heterocycle, $SO_2$—$N((CH_2)_n$-aryl)$_2$, $SO_2$—$N((CH_2)_n$-(heterocycle)$_2$ where n may be 0-6, and the aryl radical or heterocyclic radical may be substituted up to twice by F, Cl, Br, OH, $CF_3$, $NO_2$, CN, $OCF_3$, O—$(C_1$-$C_6)$-alkyl, $(C_1$-$C_6)$-alkyl, $NH_2$;

$C(NH)(NH_2)$, $NH_2$, NH—$(C_1$-$C_6)$-alkyl, $N((C_1$-$C_6)$-alkyl)$_2$, $NH(C_1$-$C_7)$-acyl, NH—CO—$(C_1$-$C_6)$-alkyl, NH—COO—$(C_1$-$C_6)$-alkyl, NH—CO-aryl, NH—CO-heterocycle, NH—COO-aryl, NH—COO-heterocycle, NH—CO—NH—$(C_1$-$C_6)$-alkyl, NH—CO—NH-aryl, NH—CO—NH-heterocycle, $N(C_1$-$C_6)$-alkyl —CO—$(C_1$-$C_6)$-alkyl, $N(C_1$-$C_6)$-alkyl —COO—$(C_1$-$C_6)$-alkyl, $N(C_1$-$C_6)$-alkyl —CO-aryl, $N(C_1$-$C_6)$-alkyl —CO-heterocycle, $N(C_1$-$C_6)$-alkyl —COO-aryl, $N(C_1$-$C_6)$-alkyl —COO-heterocycle, $N(C_1$-$C_6)$-alkyl —CO—NH—$(C_1$-$C_6)$-alkyl), $N(C_1$-$C_6)$-alkyl —CO—NH-aryl, $N(C_1$-$C_6)$-alkyl —CO—NH-heterocycle, $N((C_1$-$C_6)$-alkyl)-CO—N—$(C_1$-$C_6)$-alkyl)$_2$, $N((C_1$-$C_6)$-alkyl)-CO—N($(C_1$-$C_6)$-alkyl)-aryl, $N((C_1$-$C_6)$-alkyl)-CO—N($(C_1$-$C_6)$-alkyl)-heterocycle, $N((C_1$-$C_6)$-alkyl)-CO—N-(aryl)$_2$, $N((C_1$-$C_6)$-alkyl)-CO—N-(heterocycle)$_2$, N(aryl)-CO—$(C_1$-$C_6)$-alkyl, N(heterocycle)-CO—$(C_1$-$C_6)$-alkyl, N(aryl)-COO—$(C_1$-$C_6)$-alkyl, N(heterocycle)-COO—$(C_1$-$C_6)$-alkyl, N(aryl)-CO-aryl, N(heterocycle)-CO-aryl, N(aryl)-COO-aryl, N(heterocycle)-COO-aryl, N(aryl)-CO—NH—$(C_1$-$C_6)$-alkyl), N(heterocycle)-CO—NH—$(C_1$-$C_6)$-alkyl), N(aryl)-CO—NH-aryl, N(heterocycle)-CO—NH-aryl, N(aryl)-CO—N—$(C_1$-$C_6)$-alkyl)$_2$, N(heterocycle)-CO—N—$(C_1$-$C_6)$-alkyl)$_2$, N(aryl)-CO—N($(C_1$-$C_6)$-alkyl)-aryl, N(heterocycle)-CO—N($(C_1$-$C_6)$-alkyl)-aryl, N(aryl)-CO—N-(aryl)$_2$, N(heterocycle)-CO—N-(aryl)$_2$, aryl, O—$(CH_2)_n$-aryl, O—$(CH_2)_n$-heterocycle, where n may be 0-6, where the aryl radical or heterocyclic radical may be substituted one to 3 times by F, Cl, Br, I, OH, $CF_3$, $NO_2$, CN, $OCF_3$, O—$(C_1$-$C_6)$-alkyl, $(C_1$-$C_6)$-alkyl, $NH_2$, $NH(C_1$-$C_6)$-alkyl, $N((C_1$-$C_6)$-alkyl)$_2$, $SO_2$—$CH_3$, COOH, COO—$(C_1$-$C_6)$-alkyl, $CONH_2$.

Heterocycle or heterocyclic radical means rings and ring systems which, apart from carbon, also comprise heteroatoms such as, for example, nitrogen, oxygen or sulfur. Also included in this definition are ring systems in which the heterocycle or the heterocyclic radical is fused to benzene nuclei.

Suitable "heterocyclic rings" or "heterocyclic radicals" are acridinyl, azocinyl, benzimidazolyl, benzofuryl, benzothienyl, benzothiophenyl, benzodioxolyl, benzoxazolyl, benzthiazolyl, benztriazolyl, benztetrazolyl, benzisoxazolyl, benzisothiazolyl, benzimidazalinyl, carbazolyl, 4aH—carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl.

Pyridyl stands for 2-, 3- and 4-pyridyl. Thienyl stands both for 2- and 3-thienyl. Furyl stands both for 2- and 3-furyl.

Also included are the corresponding N-oxides of these compounds, that is to say, for example, 1-oxy-2-, 3- or 4-pyridyl.

Also included are derivatives of these heterocycles which are benzo-fused one or more times. The heterocyclic rings or heterocyclic radicals may be substituted one or more times by suitable groups such as, for example: F, Cl, Br, I, $CF_3$, $NO_2$, $N_3$, CN, COOH, COO($C_1$-$C_6$)alkyl, $CONH_2$, CONH($C_1$-$C_6$) alkyl, CON[($C_1$-$C_6$)alkyl]$_2$, cycloalkyl, ($C_1$-$C_{10}$)-alkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle;

$PO_3H_2$, $SO_3H$, $SO_2$—$NH_2$, $SO_2NH(C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, $SO_2$—N(($CH_2$)$_n$-(heterocycle)$_2$ where n may be 0-6, and the aryl radical or heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$;

C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl —CO—($C_1$-$C_6$)-alkyl, N($C_1$-$C_6$)-alkyl —COO—($C_1$-$C_6$)-alkyl, N($C_1$-$C_6$)-alkyl —CO-aryl, N($C_1$-$C_6$)-alkyl —CO-heterocycle, N($C_1$-$C_6$)-alkyl —COO-aryl, N($C_1$-$C_6$)-alkyl —COO-heterocycle, N($C_1$-$C_6$)-alkyl —CO—NH—($C_1$-$C_6$)-alkyl), N($C_1$-$C_6$)-alkyl —CO—NH-aryl, N($C_1$-$C_6$)-alkyl —CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)n-aryl, O—($CH_2$)$_n$-heterocycle, where n may be 0-6, where the aryl radical or heterocyclic radical may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$-$CH_3$, COOH, COO—($C_1$-$C_6$)-alkyl, $CONH_2$.

The amount of a compound of formula I necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of bodyweight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, capsules or tablets, may contain, for example, from 1.0 to 1000 mg, typically from 10 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contain a defined amount of the compound of formula I; as powders or granules, as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of formula I exhibit favorable effects on glucose metabolism. They are particularly suitable for the prevention and treatment of type II diabetes.

The compounds of formula I may be administered on their own, but also in combination with further active ingredients. Further active ingredients suitable for combination products are: all antidiabetics mentioned in the Rote Liste 2004, chapter 12. They may be combined with the compounds of the formula I of the invention in particular for a synergistic improvement of the effect. Administration of the active ingredient combination may take place either by separate administration of the active ingredients to the patient or in the form of combination products in which a plurality of active ingredients are present in one pharmaceutical preparation. Most of the active ingredients listed below are disclosed in the USP Dictionary of USAN and International Drug Names, US Pharmacopeia, Rockville 2001.

Antidiabetics include insulin and insulin derivatives such as, for example, Lantus® (see www.lantus.com) or Apidra®, fast-acting insulins (see U.S. Pat. No. 6,221,633), GLP-1 derivatives such as, for example, those disclosed in WO 98/08871 of Novo Nordisk A/S, and orally effective hypoglycemic active ingredients.

The orally effective hypoglycemic active ingredients include, preferably, sulfonylureas, biguanidines, meglitinides, oxadiazolidinediones, thiazolidinediones, glucosidase inhibitors, glucagon antagonists, GLP-1 agonists, potassium channel openers such as, for example, those disclosed in WO 97/26265 and WO 99/03861 of Novo Nordisk A/S, insulin sensitizers, inhibitors of liver enzymes involved in the stimulation of gluconeogenesis and/or glycogenolysis, modulators of glucose uptake, compounds which alter lipid metabolism, such as antihyperlipidemic active ingredients and antilipidemic active ingredients, compounds which reduce food intake, PPAR and PXR agonists and active ingredients which act on the ATP-dependent potassium channel of the beta cells (PPAR=peroxisome proliferator activated receptor, PXR=pregnane X receptor, ATP=adenosine triphosphate).

In one embodiment of the invention, the compounds of the formula I are administered in combination with an HMGCoA reductase inhibitor such as simvastatin, fluvastatin, pravastatin, lovastatin, atorvastatin, cerivastatin, rosuvastatin (HMG-CoA=3-hydroxy-3-methylglutaryl coenzyme A).

In one embodiment of the invention, the compounds of the formula I are administered in combination with a cholesterol absorption inhibitor such as, for example, ezetimibe, tiqueside, pamaqueside, or with a compound as described in PCT/EP 2004/00269, WO 2004/000804, WO 2004/000803, WO 2004/000805, EP 0114531, U.S. Pat. No. 6,498,156.

In one embodiment of the invention, the compounds of the formula I are administered in combination with a PPAR gamma agonist, such as, for example, rosiglitazone, pioglitazone, JTT-501, GI 262570.

In one embodiment of the invention, the compounds of the formula I are administered in combination with a PPAR alpha agonist, such as, for example, GW 9578, GW 7647.

In one embodiment of the invention, the compounds of the formula I are administered in combination with a mixed PPAR alpha/gamma agonist, such as, for example, GW 1536, AVE 8042, AVE 8134, AVE 0847, or as described in WO 00/64888, WO 00/64876, DE10142734.4.

In one embodiment of the invention, the compounds of the formula I are administered in combination with a fibrate such as, for example, fenofibrate, clofibrate, bezafibrate.

In one embodiment of the invention, the compounds of the formula I are administered in combination with an MTP inhibitor such as, for example, implitapide, BMS-201038, R-103757 (MTP=microsomal triglyceride transfer protein).

In one embodiment of the invention, the compounds of the formula I are administered in combination with bile acid absorption inhibitor (see, for example, U.S. Pat. No. 6,245,744 or U.S. Pat. No. 6,221,897), such as, for example, HMR 1741.

In one embodiment of the invention, the compounds of the formula I are administered in combination with a CETP inhibitor, such as, for example, JTT-705 (CETP=cholesteryl ester transfer protein).

In one embodiment of the invention, the compounds of the formula I are administered in combination with a polymeric bile acid adsorbent such as, for example, cholestyramine, colesevelam.

In one embodiment of the invention, the compounds of the formula I are administered in combination with an LDL receptor inducer (see U.S. Pat. No. 6,342,512), such as, for example, HMR1171, HMR1586 (LDL=low density lipids).

In one embodiment of the invention, the compounds of the formula I are administered in combination with an ACAT inhibitor, such as, for example, avasimibe (ACAT=acyl-coenzyme A:cholesterol acyltransferase).

In one embodiment of the invention, the compounds of the formula I are administered in combination with an antioxidant, such as, for example, OPC-14117.

In one embodiment of the invention, the compounds of the formula I are administered in combination with a lipoprotein lipase inhibitor, such as, for example, NO-1886.

In one embodiment of the invention, the compounds of the formula I are administered in combination with an ATP-citrate lyase inhibitor, such as, for example, SB-204990.

In one embodiment of the invention, the compounds of the formula I are administered in combination with a squalene synthetase inhibitor, such as, for example, BMS-188494.

In one embodiment of the invention, the compounds of the formula I are administered in combination with a lipoprotein (a) antagonist, such as, for example, CI-1027 or nicotinic acid. In one embodiment of the invention, the compounds of the formula I are administered in combination with a lipase inhibitor, such as, for example, orlistat.

In one embodiment of the invention, the compounds of the formula I are administered in combination with insulin.

In one embodiment, the compounds of the formula I are administered in combination with a sulfonylurea such as, for example, tolbutamide, glibenclamide, glipizide or glimepiride.

In one embodiment, the compounds of the formula I are administered in combination with a biguanide, such as, for example, metformin.

In one further embodiment, the compounds of the formula I are administered in combination with a meglitinide, such as, for example, repaglinide.

In one embodiment, the compounds of the formula I are administered in combination with a thiazolidinedione, such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl] methyl]-2,4-thiazolidinedione.

In one embodiment, the compounds of the formula I are administered in combination with an α-glucosidase inhibitor, such as, for example, miglitol or acarbose.

In one embodiment, the compounds of the formula I are administered in combination with an adenosine A1 agonist such as, for example, those described in WO 2004/003002.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with more than one of the aforementioned compounds, e.g. in combination with a sulfonylurea and metformin, with a sulfonylurea and acarbose, repaglinide and metformin, insulin and a sulfonylurea, insulin and metformin, insulin and troglitazone, insulin and lovastatin, etc. In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, (NPY=neuropeptide Y, e.g. naphthalene-1-sulfonic acid {4-[(4-aminoquinazolin-2-ylamino)methyl]cyclohexyl-methyl}amide, hydrochloride (CGP 71683A)), MC4 agonists (MC4=melanocortin 4 receptor, e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c] pyridin-5-yl)-1-(4-chlorophenyl)-2-oxoethyl]amide; (WO 01/91752)), orexin antagonists (e.g. 1-(2-methylbenzoxazol-6-yl)-3-[1,5]naphthyridin-4-ylurea, hydrochloride (SB-334867-A)), H3 agonists (H3=histamine receptor, e.g. 3-cyclohexyl-1-(4,4-dimethyl-1,4,6,7-tetrahydro-imidazo[4,5-c] pyridin-5-yl)-propan-1-one oxalic acid salt (WO 00/63208)); TNF agonists (TNF=tumor necrosis factor), CRF antagonists (CRF=corticotropin releasing factor, e.g. [2-methyl-9-(2,4,6-trimethylphenyl)-9H-1,3,9-triazafluoren-4-yl]dipropylamine (WO 00/66585)), CRF BP antagonists (CRF-BP=corticotropin releasing factor-binding protein, e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]ethanol hydrochloride (WO 01/83451)), CB1 (cannabinoid receptor 1) receptor antagonists (e.g. rimonabant or the active ingredients mentioned in WO 02/28346, MSH (melanocyte-stimulating hormone) agonists, CCK-A (CCK-A=cholecystokinin-A) agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed sertoninergic and noradrenergic compounds (e.g. WO 00/71549), 5HT agonists (serotonin mimetics), e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylamino-ethylcarbamoyl)-3,4-dihydro-1H-isoquinoline-2-carboxylic acid tertiary butyl ester (WO 01/85695)), TRH agonists (TRH=TSH releasing hormone; TSH=thyroid-stimulating hormone; thyrotropin), see, for example, EP 0 462 884, uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (DA=dopamine autoreceptor, such as, for example, bromocriptine, Doprexin), lipase/amylase inhibitors (e.g. WO 00/40569), PPAR modulators (e.g. WO 00/78312), RXR (RXR=retinoid X receptor) modulators or TR-β agonists.

In one embodiment of the invention, the other active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the other active ingredient is dexamphetamine or amphetamine.

In one embodiment, the other active ingredient is fenfluramine or dexfenfluramine.

In another embodiment, the other active ingredient is sibutramine.

In one embodiment, the other active ingredient is orlistat.

In one embodiment, the other active ingredient is mazindol or phentermine.

In a further embodiment, the other active ingredient is rimonabant.

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (September-October 2001), 18(5), 230-6.) Caromax is a carob-containing product from Nutrinova, Nutrition Specialties & Food Ingredients GmbH, Industriepark Hochst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

It will be appreciated that every suitable combination of the compounds of the invention with one or more of the aforementioned compounds and optionally one or more other pharmacologically active substances is regarded as falling within the protection conferred by the present invention.

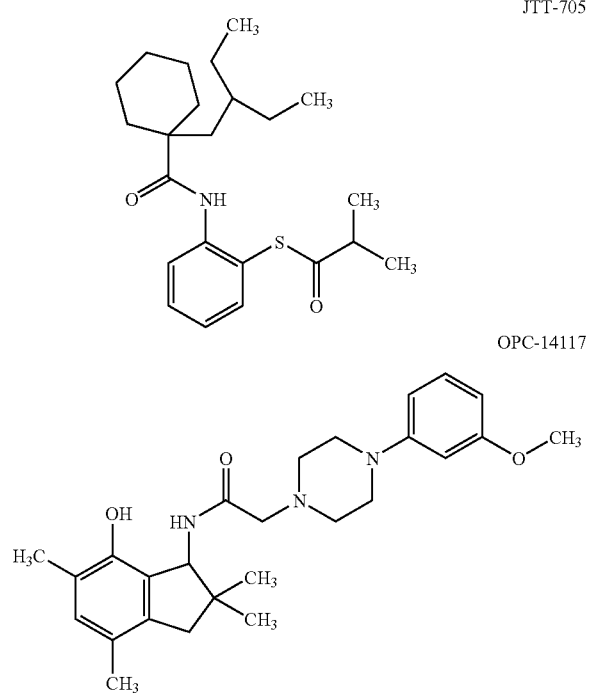

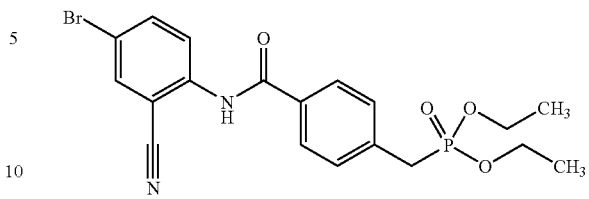

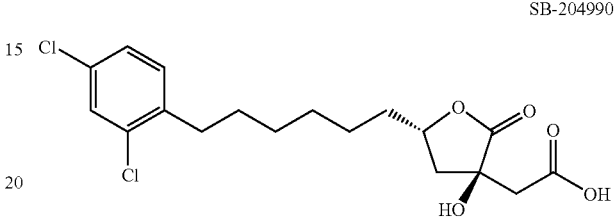

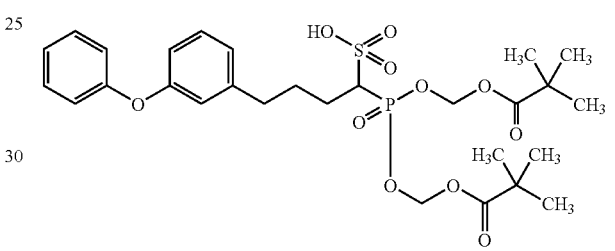

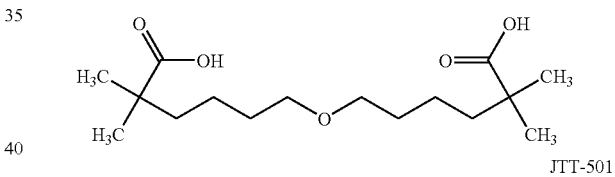

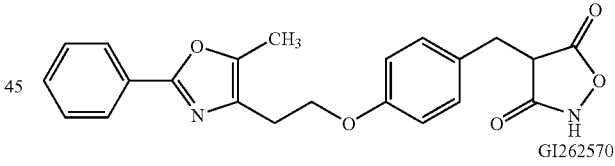

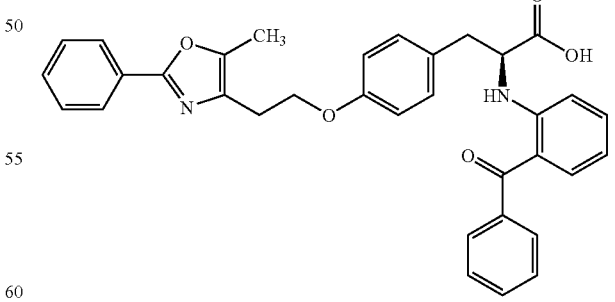

The invention also relates to processes for preparing the compounds of formula I. Suitable processes are known in principle to the skilled worker and can be found in standard works of organic chemistry. A suitable process is shown for example in scheme 1.

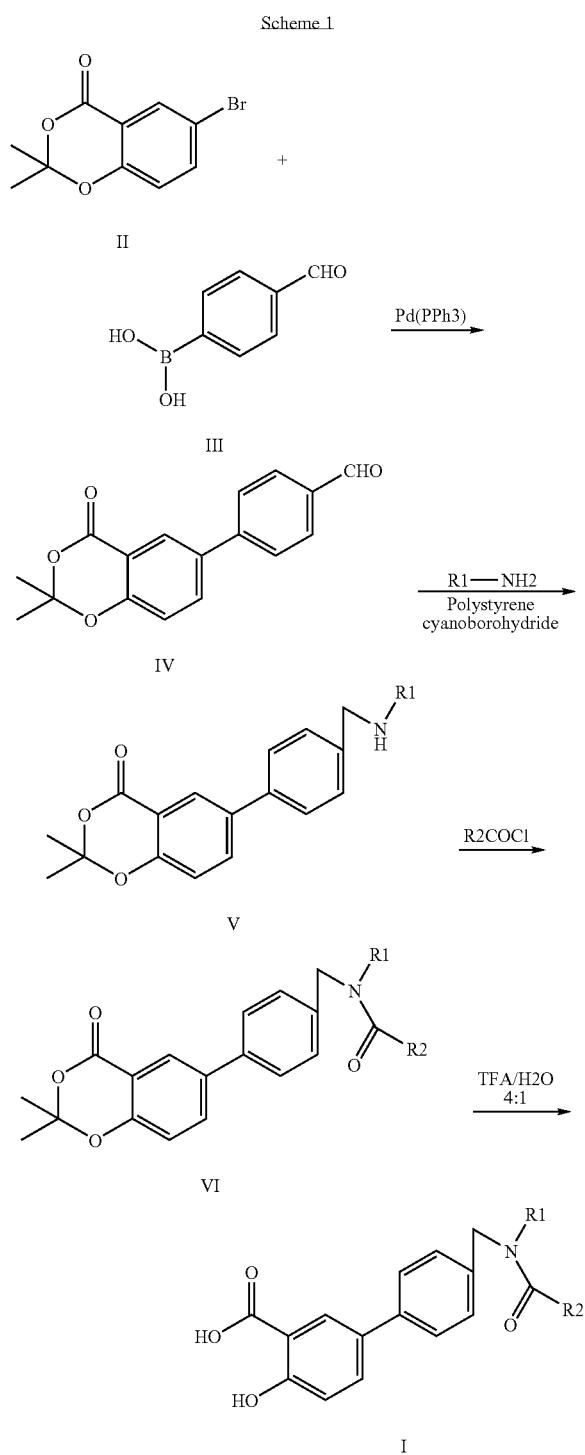

Scheme 1 tion with the acid chlorides R2COCl. Elimination of the protective groups results in a compound of the formula I.

The examples detailed below serve to illustrate the invention without, however, restricting it.

TABLE 1

I

| Ex. | R1 | R2 | A |
|---|---|---|---|
| 1 | 2-Methoxybenzyl- | 4-Bromophenyl- | Bond |
| 2 | 4-Methoxybenzyl- | 2-Benzodioxolyl- | Bond |
| 3 | Benzyl- | 2-Benzodioxolyl- | Bond |
| 4 | 2-Methoxybenzyl- | 3-Methoxyphenyl- | Bond |
| 5 | Cyclopropane-$CH_2$— | Cyclohexyl- | Bond |
| 6 | 2-Methoxybenzyl- | Cyclohexyl- | Bond |
| 7 | 4-Methylbenzyl- | 4-Bromophenyl | Bond |
| 8 | Cyclopropane-$CH_2$— | n-Butyl- | Bond |
| 9 | n-Butyl- | Cyclohexyl- | Bond |
| 10 | 4-Methylbenzyl- | Cyclohexyl- | Bond |
| 11 | Phenyl-$CH_2$—$CH_2$— | 2-Benzodioxolyl- | Bond |
| 12 | Benzyl- | 3-Methoxyphenyl | Bond |
| 13 | 4-Methylbenzyl- | 3-Methoxyphenyl | Bond |
| 14 | Cyclopropane-$CH_2$— | 2-Benzodioxolyl- | Bond |
| 15 | n-Pentyl- | 2-Benzodioxolyl- | Bond |
| 16 | 4-Fluorobenzyl- | 2-Benzodioxolyl- | Bond |
| 17 | 4-Fluorobenzyl- | 3-Methoxyphenyl | Bond |
| 18 | 4-Fluorobenzyl- | Phenyl-CH=CH— | Bond |
| 19 | 4-Methylbenzyl- | 2-Benzodioxolyl- | Bond |
| 20 | Cyclopentyl- | 2-Benzodioxolyl- | Bond |
| 21 | Benzyl- | 4-Bromophenyl- | Bond |
| 22 | Benzyl- | 2-Furanyl- | Bond |
| 23 | 4-Fluorobenzyl | 4-Bromophenyl- | Bond |
| 24 | 4-Methoxybenzyl- | n-Butyl- | Bond |

The preparation of some examples from table 1 is described in detail below, the other compounds of the formula I were obtained analogously:

4-(2,2-Dimethyl-4-oxo-4H-benzo[1,3]dioxin-6-yl)-benzaldehyde

IV

A mixture of 6-bromo-2,2-dimethyl-2,2-benzo[1,3]dioxin-4-one (1 g, 4.2 mmol) and potassium carbonate (4.5 g, 32.8 mmol, 8 eq) were diluted with THF (64 ml) and stirred at 25° C. for 15 min. The reaction vessel was flushed with $N_2$ and evacuated (5×). The mixture was stirred under an $N_2$ atmosphere for a further 15 min. In another reaction flask, 4-formyl-phenylboronic acid (0.6 g, 4 mmol) was dissolved in THF (34 ml) and degassed (×5). Pd(PPh$_3$)$_4$ (140 mg, 0.012 mol) was added to the first flask, and this solution was also degassed again (×1). The boronic acid (reaction vessel 2) was introduced in portions by a needle into the reaction mixture over a period of 2.5 h (30 min between each addition). The mixture was heated under reflux for 15 h, and the reaction was The basic building block is formed by aldehyde of a protected hydroxybiphenylcarboxylic acid of the formula IV, which is prepared by reacting a bromide of the formula II with an aldehyde of the formula III. A radical R1, which has the meaning indicated above in formula I, is introduced by reacting the appropriate R1-amines with reductive amination of the CHO group. A radical R2, which has the meaning indicated above in formula I, is introduced by subsequent amidafollowed by thin-layer chromatography. The mixture was cooled, filtered through kieselguhr and washed with EtOAc. The filtrate was concentrated in vacuo, and the residue was purified by flash chromatography (1:9, ethyl acetate/hexane).

Yield: (519 mg, 46%).

General Method for the Reductive Amination

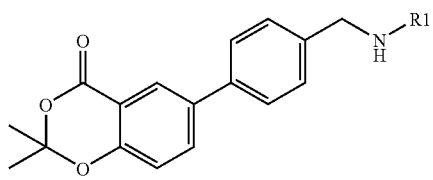

V

Biarylaldehyde ((56.4 mg, 0.2 mmol), the appropriate amine (0.24 mmol, 1.2 equiv) and THF/MeOH (1:2, 10 ml) was introduced into a carousel of reaction vessels. Glacial acetic acid (12 mg, 0.2 mmol) and polystyrene cyanoborohydride (120 mg, 2.5 mmol/g, 1.5 eq.) were added to the mixtures, and they were stirred at 50° C. for 24 h. They were then quenched with 4-alkoxybenzaldehyde scavenger resin (2.5 mmol/g, 4 equivalents), and the mixtures were stirred at 25° C. for 16 h. The reactions were followed by thin-layer chromatography (15:1 dichloromethane/methanol; 2 drops of triethylamine). The mixtures were filtered and washed with dichloromethane. The crude products were reacted further without further purification.

General Method for Parallel Amidation

The amines (crude products; ~0.2 mmol, 1 eq) were dissolved in THF (2 ml), and Amberlite IRA 400-$CO_3{}^2$ (2.5 mmol/g, 1.5 eq) was added to the solutions. Solutions of the appropriate acid chlorides (0.24 mmol) in THF (2 ml) were added to these reaction mixtures, and the mixtures were shaken at 25° C. for 16 h. The resins were filtered off, and the solvent was distilled off in vacuo. The residues were taken up in EtOAc and washed with saturated $NaHCO_3$ solution. The organic phases were dried ($Na_2SO_4$) and the solvent was distilled off in vacuo. The amides were reacted further without further purification.

General Method for Protective Group Elimination

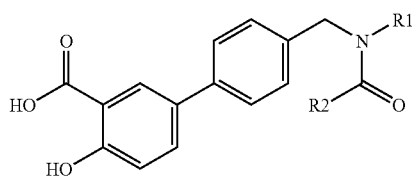

I

The amides from the preceding stage are taken up in 4:1 trifluoroacetic acid/water (5 ml) and stirred at 25° C. for 15 h. The solvent is distilled off, and the crude products are purified by preparative HPLC.

Preparation of Amberlite IRA-400 Cyanoborohydride 100 ml of an aqueous sodium cyanoborohydride solution (8% w/vol, slightly cloudy) is put onto 10 g of moist Amberlite IRA 100 resin (chloride form) in a frit. The resin is stirred and then filtered off with suction. The process is repeated 10×. The resin treated in this way is carefully washed with water until it is free of excess sodium cyanoborohydride (pH check) and is then dried by repeated washing with tetrahydrofuran.

The average capacity is 2.5 mmol/g of dry resin.

Preparation of Amberlite IRA-400 Carbonate

Amberlite IRA 400 (Cl⁻) resin is treated in analogy to the above method with a solution of sodium carbonate (10 g) in water (100 ml) and then washed with water until neutral.

The following examples were prepared by this method, and the identity was verified by mass spectrometry:

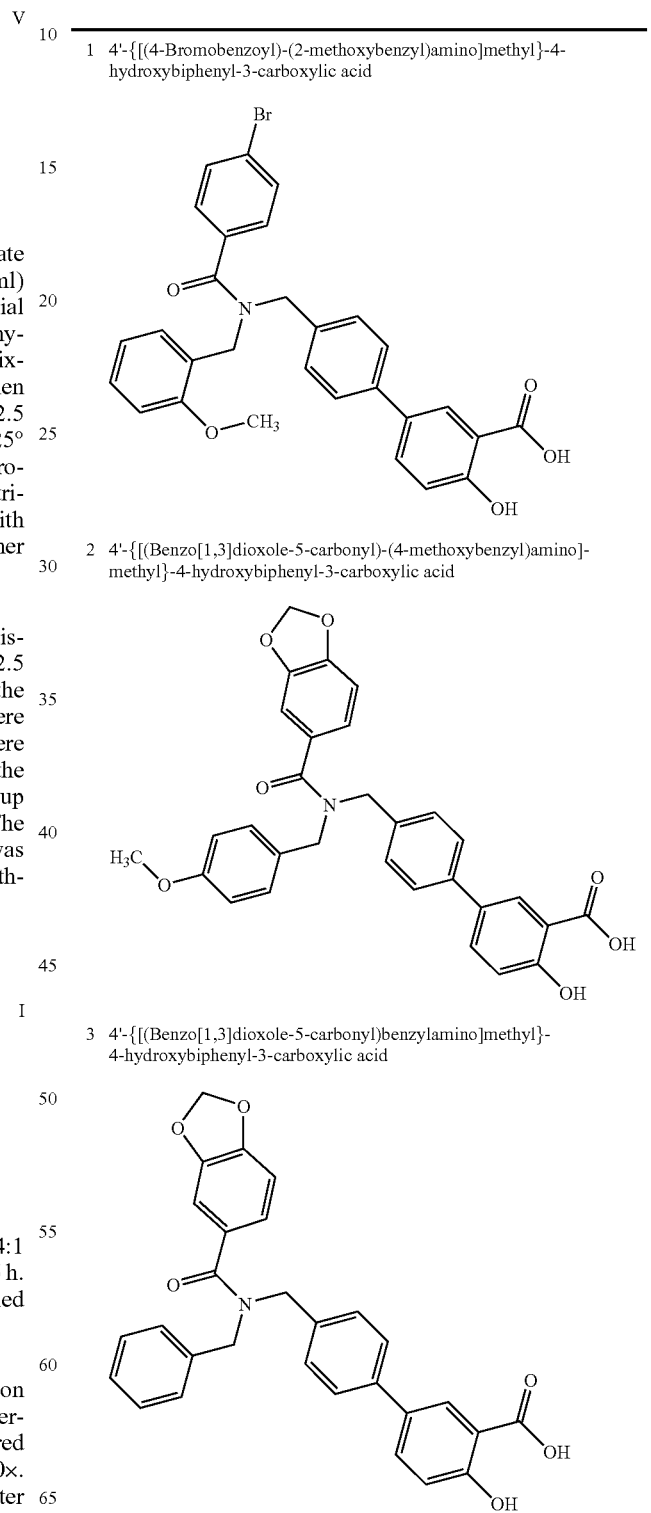

1  4'-{[(4-Bromobenzoyl)-(2-methoxybenzyl)amino]methyl}-4-hydroxybiphenyl-3-carboxylic acid 2  4'-{[(Benzo[1,3]dioxole-5-carbonyl)-(4-methoxybenzyl)amino]-methyl}-4-hydroxybiphenyl-3-carboxylic acid 3  4'-{[(Benzo[1,3]dioxole-5-carbonyl)benzylamino]methyl}-4-hydroxybiphenyl-3-carboxylic acid

| | |
|---|---|
| 4 | 4-Hydroxy-4'-{[(3-methoxybenzoyl)-(2-methoxybenzyl)amino]-methyl}biphenyl-3-carboxylic acid 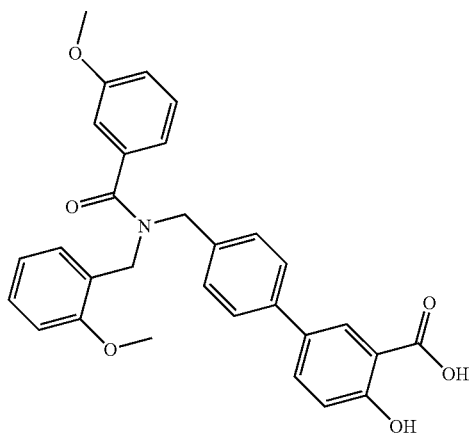 |
| 5 | 4'-[(Cyclohexanecarbonylcyclopropylmethylamino)methyl]-4-hydroxybiphenyl-3-carboxylic acid 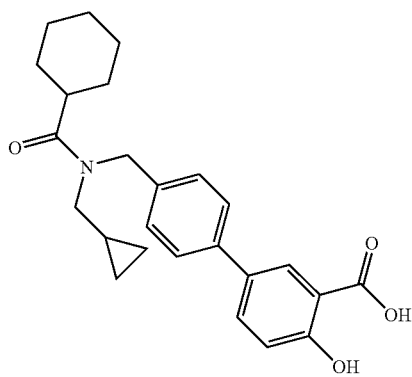 |
| 6 | 4'-{[Cyclohexanecarbonyl-(2-methoxybenzyl)amino]methyl}-4-hydroxybiphenyl-3-carboxylic acid 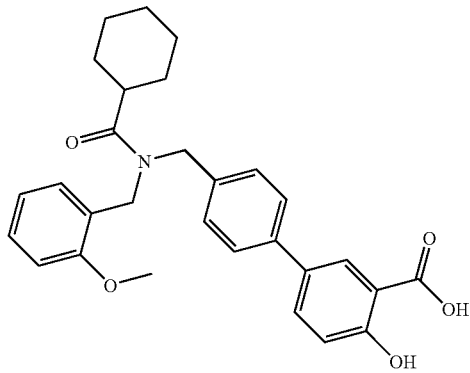 |
| 7 | 4'-{[(4-Bromobenzoyl)-(4-methylbenzyl)amino]methyl}-4-hydroxybiphenyl-3-carboxylic acid 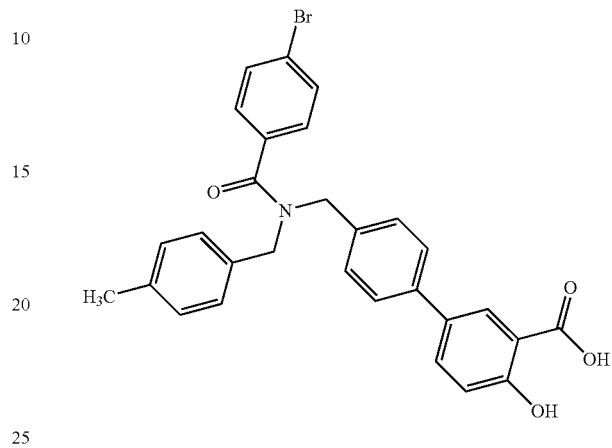 |
| 8 | 4'-[(Cyclopropylmethylpentanoylamino)methyl]-4-hydroxybiphenyl-3-carboxylic acid 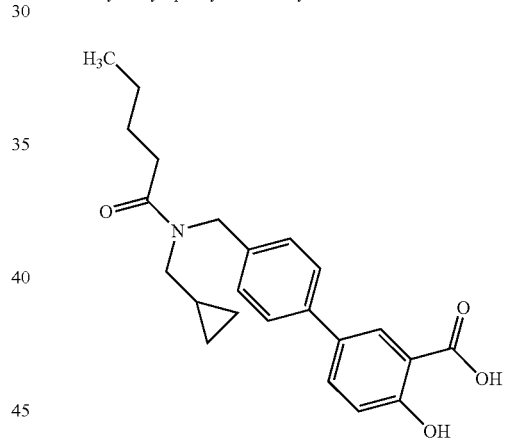 |
| 9 | 4'-[(Cyclohexanecarbonylpentylamino)methyl]-4-hydroxybiphenyl-3-carboxylic acid 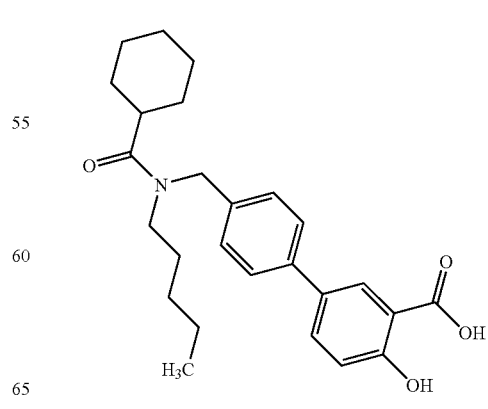 |

10  4'-{[Cyclohexanecarbonyl-(4-methylbenzyl)amino]methyl}-4-hydroxybiphenyl-3-carboxylic acid

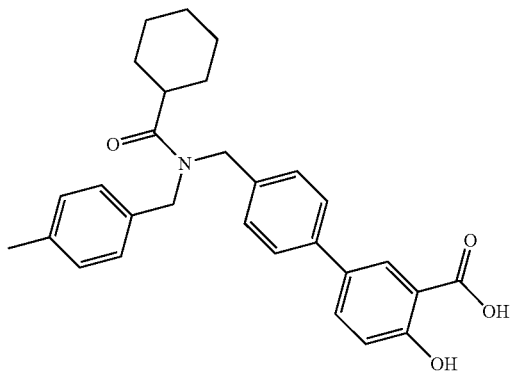

11  4'-{[(Benzo[1,3]dioxole-5-carbonyl)phenethylamino]methyl}-4-hydroxybiphenyl-3-carboxylic acid

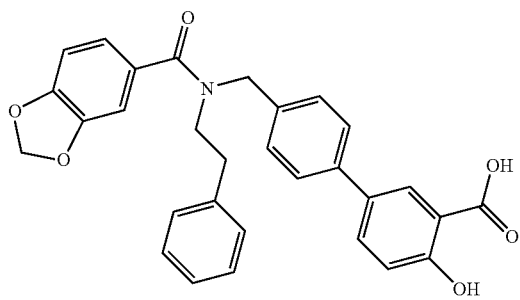

12  4'-{[Benzyl-(3-methoxybenzoyl)amino]methyl}-4-hydroxybiphenyl-3-carboxylic acid

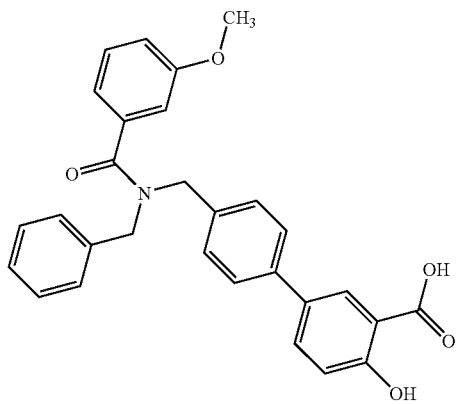

13  4-Hydroxy-4'-{[(3-methoxybenzoyl)-(4-methylbenzyl)amino]methyl}-biphenyl-3-carboxylic acid

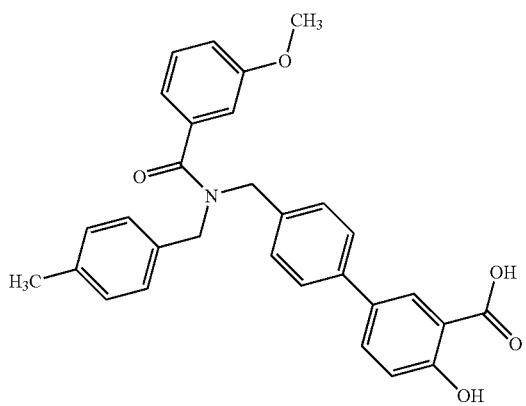

14  4'-{[(Benzo[1,3]dioxole-5-carbonyl)cyclopropylmethylamino]methyl}-4-hydroxybiphenyl-3-carboxylic acid

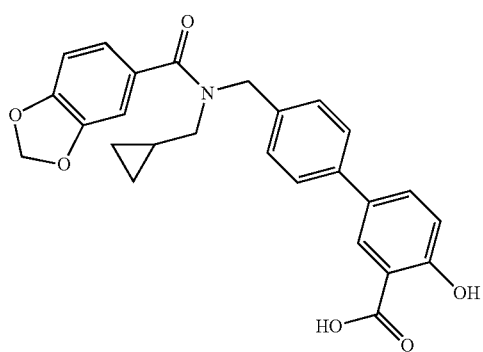

15  4'-{[(Benzo[1,3]dioxole-5-carbonyl)pentylamino]methyl}-4-hydroxybiphenyl-3-carboxylic acid

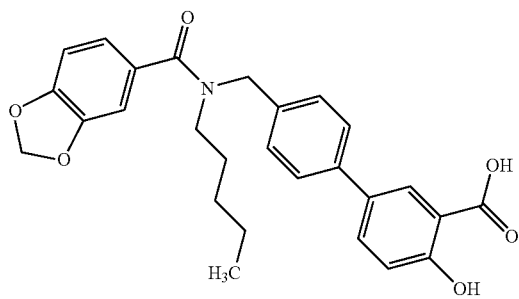

-continued 16 4'-{[(Benzo[1,3]dioxole-5-carbonyl)-(4-fluorobenzyl)amino]methyl}-4-hydroxy-biphenyl-3-carboxylic acid

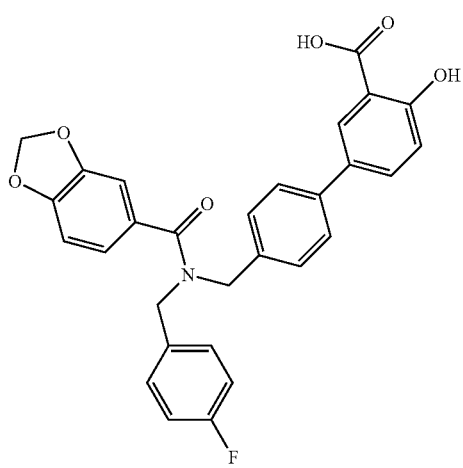

17 4'-{[(4-Fluorobenzyl)-(3-methoxybenzoyl)amino]methyl}-4-hydroxybiphenyl-3-carboxylic acid

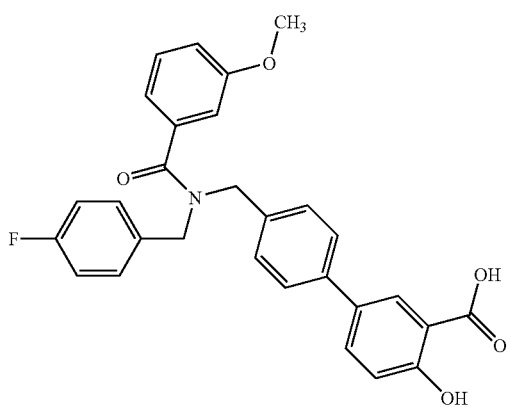

18 4'-{[(4-Fluorobenzyl)-(3-phenylacryloyl)amino]methyl}-4-hydroxybiphenyl-3-carboxylic acid

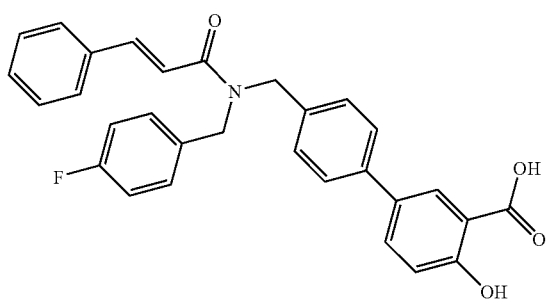

-continued 19 4'-{[(Benzo[1,3]dioxole-5-carbonyl)-(4-methylbenzyl)amino]methyl}-4-hydroxy-biphenyl-3-carboxylic acid

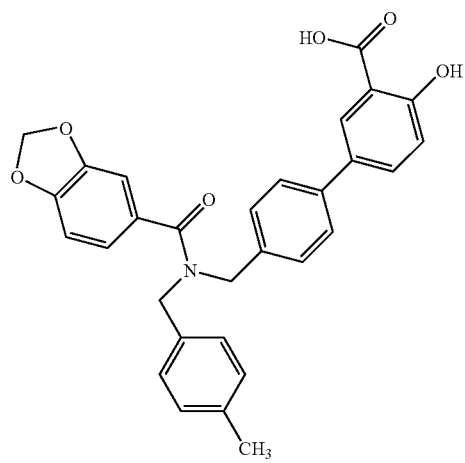

20 4'-{[(Benzo[1,3]dioxole-5-carbonyl)cyclopentylamino]methyl}-4-hydroxy-biphenyl-3-carboxylic acid

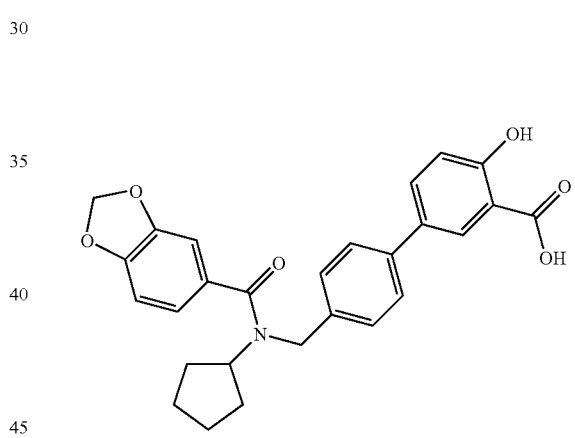

21 4'-{[Benzyl-(4-bromobenzoyl)amino]methyl}-4-hydroxybiphenyl-3-carboxylic acid

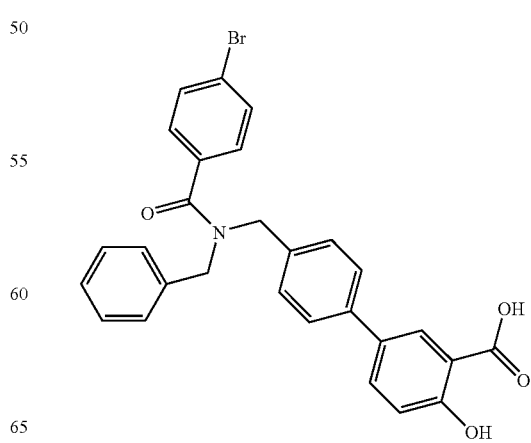

-continued 22 4'-{[Benzyl(furan-2-carbonyl)amino]methyl}-4-hydroxybiphenyl-3-carboxylic acid

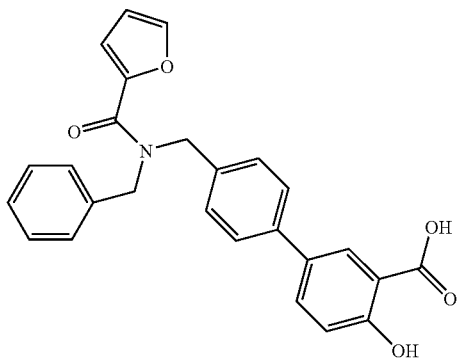

23 4'-{[(4-Bromobenzoyl)-(4-fluorobenzyl)amino]methyl}-4-hydroxybiphenyl-3-carboxylic acid

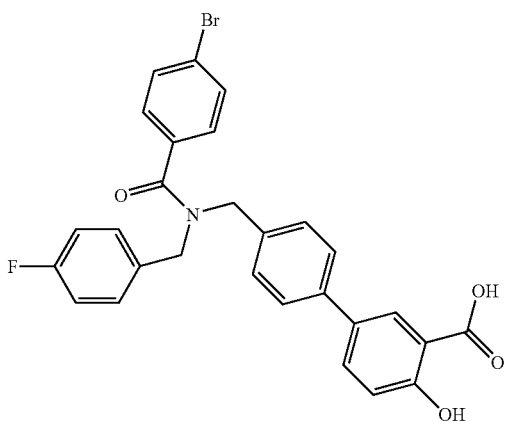

24 4-Hydroxy-4'-{[(4-methoxybenzyl)pentanoylamino]methyl}-biphenyl-3-carboxylic acid

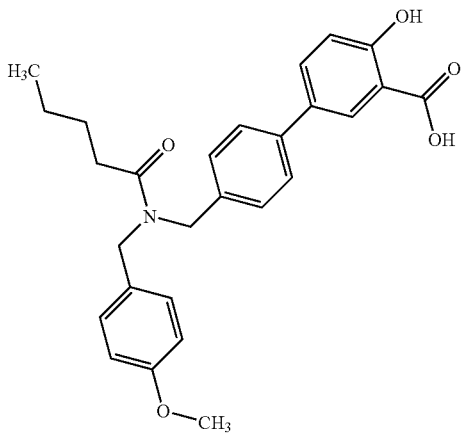

The activity of the compounds was tested as follows:

Enzymatic Test Systems for Detecting Inhibition of a Phosphatase

The compounds of the formula I were tested for their phosphatase-inhibiting effect in an in vitro assay. The enzyme preparation and the performance of the assay was carried out as follows.

Obtaining the Enzyme Preparation:

A) Cell Culture:

Sf9 cells (=*Spodoptera frugiperda* cell type; obtainable from invitrogen) are cultured in Grace's supplemented medium (Gibco-BRL) with 10% heat-inactivated fetal calf serum (Gibco-BRL) in spinner flasks at 28° C. in accordance with the protocol of Summers and Smith (A Manual for Methods for Baculovirus Vectors and Insect Culture Procedures [Bulletin No. 15555]. Texas A & M University, Texas Agricultural Experiment Station, College Station, Tex., 1987).

Construction of recombinant Baculovirus transfer vectors: cDNA coding for the regulatory and catalytic domains of human PTP1B, but without the carboxy-terminal hydrophobic region (corresponding to 1-299 aa) was obtained by polymerase chain reaction via primers with attached cloning sites and suitable cDNA templates (obtainable for example from invitrogen) and then cloned into baculovirus expression vectors (Amersham Pharmacia Biotech.). The recombinant baculoviruses were prepared with the aid of the Bac-to-Bac baculovirus expression system (obtainable from Gibco-BRL). The gene was cloned into the pFASTBAC donor plasmid (obtainable from Life Technologies). The resulting plasmid was transformed into competent DH10BAC *Escherichia coli* cells (obtainable from Life Technologies). After transposition and antibiotic selection, the recombinant plasmid DNA was isolated from selected *E. coli* colonies and then used for the transfection of Sf9 insect cells. The virus particle in the supernatant medium was amplified three times up to a viral stock volume of 500 ml.

B) Production of Recombinant Protein:

Baculovirus infection of a 500 ml spinner culture of Sf9 cells was essentially carried out as described by Summers and Smith (see above). Sf9 cells at a density of $1-3 \times 10^6$ cells/ml were pelleted by centrifugation at 300 g for 5 min, the supernatant was removed, and the cells were resuspended in a density of $1 \times 10^7$ cells/ml in a suitable recombinant viral stock (MOI 10). After careful shaking at room temperature for 1.5 h, fresh medium was added in order to achieve a cell density of $1 \times 10^6$ cells/ml. The cells were then cultured in the suspension at 28° C. for suitable periods after postinfection.

C) Cellular Fractionation and Complete Cell Extracts of Infected Sf9 Cells:

After the postinfection, aliquots were subjected to an analysis of protein expression by SDS-PAGE and Western blot analysis. The cellular fractionation was carried out as described (Cromlish, W. and Kennedy, B. Biochem. Pharmacol. 52: 1777-1785, 1996). Complete cell extracts were obtained from 1 ml aliquots of the infected Sf9 cells after certain times postinfection. The pelleted cells (300×g, 5 min) were washed once in phosphate-buffered saline (4° C.), resuspended in 50 µl of water and disrupted by repeated freezing/thawing. Protein concentrations were determined with the aid of the Bradford method and bovine serum albumin as standard.

Assay Procedure:

A) Dephosphorylation of a Phosphopeptide:

This assay is based on the release of phosphate from a consensus substrate peptide which is detected in the nanomolar concentration range by the malachite green/ammonium molybdate method (Lanzetta, P. A., Alvarez, L. J., Reinach, P. S., Candia, O. A. Anal Biochem. 100: 95-97, 1979) adapted for the microtiter plate format. The dodecatrisphosphopeptide TRDIYETDYYRK (Biotrend, Cologne) corresponds to amino acids 1142-1153 of the catalytic domain of the insulin receptor and is (auto)phosphorylated on tyrosine residues 1146, 1150 and 1151. The recombinant hPTP1B was diluted with assay buffer (40 mM Tris/HCl, pH 7.4, 1 mM EDTA, 20 mM DTT), equivalent to an activity of 1000-1500 nmol/min/mg of protein and (a 20 µl portion) then preincubated (15 min, 30° C.) in the absence or presence of test substance (5 µl) in the desired concentration (final concentration of DMSO 2% max.) in a total volume of 90 µl (assay buffer). To start the dephosphorylation reaction, the peptide substrate (10 µl, prewarmed to 30° C.) was added to the preincubated enzyme preparation with or without test substance (final concentration 0.2-200 µM) and the incubation was continued for 1 h. The reaction was stopped by adding 100 µl of malachite green hydrochloride (0.45%, 3 parts), ammoniummolybdatetetrahydrate (4.2% in 4 N HCl, 1 part) and 0.5% Tween 20 as stop solution. After incubation at 22° C. for 30 min to develop the color, the absorption at 650 nm was determined using a microtiter plate reader (molecular devices). Samples and blanks were measured in triplicate. The PTP1B activity was calculated as nanomoles of liberated phosphate per min and mg of protein with potassium phosphate as standard. The inhibition of the recombinant hPTP1B by test substances was calculated as a percentage of the phosphatase control. The $IC_{50}$ values show significant agreement with a four-parameter non-linear logistic regression curve.

B) Cleavage of P-Nitrophenyl Phosphate:

This assay is based on the change in absorption of the non-physiological substrate p-nitrophenyl phosphate during cleavage to give nitrophenol under standard conditions (Tonks, N. K., Diltz, C. D:, Fischer, E. H. J. Biol. Chem. 263: 6731-6737, 1988; Burke T. R., Ye, B., Yan, X. J., Wang, S. M., Jia, Z. C., Chen, L., Zhang, Z. Y., Barford, D. Biochemistry 35: 15989-15996, 1996). The inhibitors are pipetted in suitable dilution into the reaction mixtures which contain 0.5-5 mM p-nitrophenyl phosphate. The following buffers were used (total volume 100 µl): (a) 100 mM sodium acetate (pH 5.5), 50 mM NaCl, 0.1% (w/v) bovine serum albumin, 5 mM glutathione, 5 mM DTT, 0.4 mM EGTA and 1 mM EDTA; (b) 50 mM Hepes/KOH (pH 7.4), 100 mM NaCl, 0.1% (w/v) bovine serum albumin, 5 mM glutathione, 5 mM DTT and 1 mM EDTA. The reaction was started by adding enzyme and carried out in microtiter plates at 25° C. for 1 h. The reaction was stopped by adding 100 µl of 0.2 N NaOH. The enzyme activity was determined by measuring the absorption at 405 nm with suitable corrections for absorption of the test substances and of p-nitrophenyl phosphate. The results were expressed as percentage of the control by comparing the amount of p-nitrophenol formed in the test substance-treated samples (nmol/min/mg of protein) with the amount in the untreated samples. The average and the standard deviation were calculated, and the IC50 values were determined by regression analysis of the linear portion of the inhibition curves.

TABLE 3

| Ex. | Biological activity IC-50 (µM) |
|---|---|
| 1 | 1.2 |
| 2 | 1.2 |
| 3 | 1.5 |
| 4 | 1.4 |
| 5 | 1.6 |
| 6 | 1.3 |
| 7 | 1 |
| 8 | 1.9 |
| 9 | 1.6 |
| 10 | 1.6 |
| 11 | 1.6 |
| 12 | 1.6 |
| 13 | 1.7 |
| 14 | 1.8 |
| 15 | 1.5 |
| 16 | 1.9 |
| 17 | 1.6 |
| 18 | 1.45 |
| 19 | 1.28 |
| 20 | 1.8 |
| 21 | 0.6 |
| 22 | 1.3 |
| 23 | 0.5 |
| 24 | 0.6 |

It is evident from the table that the compounds of the formula I inhibit the activity of phosphotyrosine phosphatase 1B (PTP1B) and thus are very suitable for lowering the blood glucose level. They are therefore suitable in particular for the treatment of type I and II diabetes, of insulin resistance, of dyslipidemias, of the metabolic syndrome/syndrome X, of pathological obesity and for weight reduction in mammals.

Compounds of the formula I are also suitable, because of their inhibition of PTP1B, for the treatment of hyperglycerimia, high blood pressure, atherosclerosis, dysfunctions of the immune system, autoimmune diseases, allergic diseases such as, for example, asthma, arthritis, osteoarthritis, osteoporosis, proliferation disorders such as cancer and psoriasis, diseases with reduced or increased production of growth factors, hormones or cytokines, which induce the release of growth hormones.

The compounds are also suitable for the treatment of disorders of the nervous system such as, for example, Alzheimer's or multiple sclerosis.

The compounds are also suitable for the treatment of disturbances of wellbeing and other psychiatric indications such as, for example, depressions, anxiety states, anxiety neuroses, schizophrenia, for the treatment of disorders associated with the circadian rhythm and for the treatment of drug abuse.

They are additionally suitable for treatment of sleep disorders, sleep apnea, female and male sexual disorders, inflammations, acne, pigmentation of the skin, disorders of steroid metabolism, skin diseases and mycoses.

The invention claimed is:

1. A compound of the formula I,

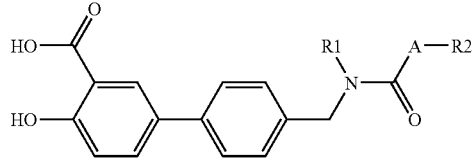

in which:

R1 is selected from —($C_1$-$C_6$)-alkyl, —($C_1$-$C_4$)-alkyl-O—($C_1$-$C_4$)-alkyl, —($C_2$-$C_6$)-alkenyl, —($C_3$-$C_8$)-cycloalkyl, -aryl, —($C_1$-$C_6$)-alkyl-aryl, —($C_2$-$C_6$)-alkenyl-aryl, —($C_1$-$C_6$)-alkyl-cycloalkyl, and —($C_2$-$C_6$)-alkenyl-cycloalkyl, where the alkyl, alkenyl, aryl and cycloalkyl radicals may be substituted by a substituent selected from F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-aryl, and O—CO—($C_1$-$C_6$)-heterocycle; as well as $PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, $SO_2$—N(($CH_2$)$_n$-(heterocycle)$_2$ where n may be 0-6, and the aryl radical or heterocyclic radical may be substituted up to twice by a substituent selected from F, Cl, Br, OH, $CF_3$, $NO_2$, CN, $OCF_3$, O—($C_1$-$C_6$)-alkyl, ($C_1$-$C_6$)-alkyl, $NH_2$;

C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl —CO—($C_1$-$C_6$)-alkyl, N($C_1$-$C_6$)-alkyl —COO—($C_1$-$C_6$)-alkyl, N($C_1$-$C_6$)-alkyl —CO-aryl, N($C_1$-$C_6$)-alkyl —CO-heterocycle, N($C_1$-$C_6$)-alkyl —COO-aryl, N($C_1$-$C_6$)-alkyl —COO-heterocycle, N($C_1$-$C_6$)-alkyl —CO—NH—($C_1$-$C_6$)-alkyl), N($C_1$-$C_6$)-alkyl —CO—NH-aryl, N($C_1$-$C_6$)-alkyl —CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl, and O—($CH_2$)$_n$-heterocycle, where n may be 0-6, where the aryl radical or heterocyclic radical may be substituted one to 3 times by a substituent selected from F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, and $CONH_2$;

R2 is selected from —($C_1$-$C_6$)-alkyl, —($C_1$-$C_4$)-alkyl-O—($C_1$-$C_4$)-alkyl, —($C_2$-$C_6$)-alkenyl, —($C_3$-$C_8$)-cycloalkyl, —($C_1$-$C_6$)-alkyl-aryl, —($C_2$-$C_6$)-alkenyl-aryl, heterocycle, —($C_1$-$C_6$)-alkyl-heterocycle, —($C_2$-$C_6$)-alkenyl-heterocycle, —($C_1$-$C_6$)-alkyl-cycloalkyl, and —($C_2$-$C_6$)-alkenyl-cycloalkyl, where the alkyl, alkenyl, aryl, heterocyclyl and cycloalkyl radicals may be substituted by a substituent selected from F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-aryl, and O—CO—($C_1$-$C_6$)-heterocycle; as well as $PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, and $SO_2$—N(($CH_2$)$_n$-(heterocycle)$_2$, where n may be 0-6, and the aryl radical or heterocyclic radical may be substituted up to twice by a substituent selected from F, Cl, Br, OH, $CF_3$, $NO_2$, CN, $OCF_3$, O—($C_1$-$C_6$)-alkyl, ($C_1$-$C_6$)-alkyl, and $NH_2$; as well as C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl —CO—($C_1$-$C_6$)-alkyl, N($C_1$-$C_6$)-alkyl —COO—($C_1$-$C_6$)-alkyl, N($C_1$-$C_6$)-alkyl —CO-aryl, N($C_1$-$C_6$)-alkyl —CO-heterocycle, N($C_1$-$C_6$)-alkyl —COO-aryl, N($C_1$-$C_6$)-alkyl —COO-heterocycle, N($C_1$-$C_6$)-alkyl —CO—NH—($C_1$-$C_6$)-alkyl), N($C_1$-$C_6$)-alkyl —CO—NH-aryl, N($C_1$-$C_6$)-alkyl —CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl, and O—($CH_2$)$_n$-heterocycle, where n may be 0-6, where the aryl radical or heterocyclic radical may be substituted one to 3 times by a substituent selected from F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, and $CONH_2$;

A is selected from a bond, O, NH, and S;
and the physiologically tolerated salts thereof.

2. A compound of the formula I as claimed in claim 1, wherein R1 is selected from —$(C_1$-$C_6)$-alkyl, —$(C_1$-$C_4)$-alkyl-O—$(C_1$-$C_4)$-alkyl, —$(C_2$-$C_6)$-alkenyl, —$(C_3$-$C_8)$-cycloalkyl, -aryl, —$(C_1$-$C_6)$-alkyl-aryl, —$(C_2$-$C_6)$-alkenyl-aryl, —$(C_1$-$C_6)$-alkyl-cycloalkyl, and —$(C_2$-$C_6)$-alkenyl-cycloalkyl, where the alkyl, alkenyl, aryl and cycloalkyl radicals may be substituted by a substituent selected from F, Cl, Br, I, $(C_1$-$C_6)$alkyl, O—$(C_1$-$C_6)$-alkyl;

R2 is selected from —$(C_1$-$C_6)$-alkyl, —$(C_1$-$C_4)$-alkyl-O—$(C_1$-$C_4)$-alkyl, —$(C_2$-$C_6)$-alkenyl, —$(C_3$-$C_8)$-cycloalkyl, —$(C_1$-$C_6)$-alkyl-aryl, —$(C_2$-$C_6)$-alkenyl-aryl, heterocycle, —$(C_1$-$C_6)$-alkyl-heterocycle, —$(C_2$-$C_6)$-alkenyl-heterocycle, —$(C_1$-$C_6)$-alkyl-cycloalkyl, and —$(C_2$-$C_6)$-alkenyl-cycloalkyl, where the alkyl, alkenyl, aryl, heterocyclyl and cycloalkyl radicals may be substituted by a substituent selected from F, Cl, Br, I, $(C_1$-$C_6)$alkyl, and O—$(C_1$-$C_6)$-alkyl; and A is a bond;
and the physiologically tolerated salts thereof.

3. A compound of the formula I as claimed in claim 1, wherein:

R1 is selected from —$(C_1$-$C_6)$-alkyl, —$(C_1$-$C_6)$-alkyl-phenyl, —$(C_1$-$C_6)$-alkyl-$(C_3$-$C_8)$-cycloalkyl, and —$(C_3$-$C_8)$-cycloalkyl, where the alkyl, phenyl and cycloalkyl radicals may be substituted by a substituent selected from F, Cl, Br, I, $(C_1$-$C_6)$alkyl, and O—$(C_1$-$C_6)$-alkyl;

R2 is selected from —$(C_1$-$C_6)$-alkyl, —$(C_1$-$C_6)$-alkyl-phenyl, —$(C_1$-$C_6)$-alkyl-$(C_3$-$C_8)$-cycloalkyl, —$(C_3$-$C_8)$ cycloalkyl, —$(C_2$-$C_6)$-alkenyl-phenyl, and -heterocycle, where the alkyl, phenyl, heterocyclyl and cycloalkyl radicals may be substituted by a substituent selected from F, Cl, Br, I, $(C_1$-$C_6)$alkyl, and O—$(C_1$-$C_6)$-alkyl; and A is a bond;
and the physiologically tolerated salts thereof.

4. A compound of the formula I as claimed in claim 1, wherein

R1 is selected from —$CH_2$-phenyl, —$CH_2$—$(C_3$-$C_8)$-cycloalkyl, —$(C_3$-$C_8)$-cycloalkyl, where the phenyl and cycloalkyl radicals may be substituted by F, Cl, Br, I, $(C_1$-$C_6)$alkyl, and O—$(C_1$-$C_6)$-alkyl;

R2 is selected from —$CH_2$-phenyl, —$CH_2$—$(C_3$-$C_8)$-cycloalkyl, —$(C_3$-$C_8)$-cycloalkyl, —$(C_2$-$C_6)$-alkenyl-phenyl, —$CH_2$-heterocycle, -heterocycle, where the phenyl, heterocyclyl and cycloalkyl radicals may be substituted by F, Cl, Br, I, $(C_1$-$C_6)$alkyl, O—$(C_1$-$C_6)$-alkyl; and A is a bond;
and the physiologically tolerated salts thereof.

5. A pharmaceutical composition comprising at least one compound as claimed in claim 1.

6. The pharmaceutical composition of claim 5 further comprising at least one other pharmaceutically active ingredient.

7. A pharmaceutical composition as claimed in claim 6, wherein the other active ingredient comprises one or more antidiabetics, hypoglycemic active ingredients, HMGCoA reductase inhibitors, cholesterol absorption inhibitors, PPAR gamma agonists, PPAR alpha agonists, PPAR alpha/gamma agonists, fibrates, MTP inhibitors, bile acid absorption inhibitors, CETP inhibitors, polymeric bile acid adsorbents, LDL receptor inducers, ACAT inhibitors, antioxidants, lipoprotein lipase inhibitors, ATP-citrate lyase inhibitors, squalene synthetase inhibitors, lipoprotein(a) antagonists, lipase inhibitors, insulins, sulfonylureas, biguanides, meglitinides, thiazolidinediones, α-glucosidase inhibitors, active ingredients which act on the ATP-dependent potassium channel of the beta cells, CART agonists, NPY agonists, MC4 agonists, orexin agonists, H3 agonists, TNF agonists, CRF agonists, CRF BP antagonists, urocortin agonists, β3 agonists, MSH (melanocyte-stimulating hormone) agonists, CCK agonists, serotonin reuptake inhibitors, mixed sertoninergic and noradrenergic compounds, 5HT agonists, bombesin agonists, galanin antagonists, growth hormones, growth hormone-releasing compounds, TRH agonists, uncoupling protein 2 or 3 modulators, leptin agonists, DA agonists (bromocriptine, Doprexin), lipase/amylase inhibitors, PPAR modulators, RXR modulators or TR-β agonists or amphetamines.

8. A method for reducing blood glucose comprising administering to a patient in need thereof an effective amount of a compound of claim 1.

9. A method for the treatment of type II diabetes comprising administering to a patient in need thereof an effective amount of a compound of claim 1.

10. A method for the treatment of obesity comprising administering to a patient in need thereof an effective amount of a compound of claim 1.

11. A method for the treatment of insulin resistance comprising administering to a patient in need thereof an effective amount of a compound of claim 1.

* * * * *